(12) United States Patent
Grenz et al.

(10) Patent No.: US 9,707,400 B2
(45) Date of Patent: Jul. 18, 2017

(54) SYSTEMS, METHODS, AND INTERFACES FOR CONFIGURING CARDIAC THERAPY

(71) Applicant: Medtronic, Inc., Minneapolis, MN (US)

(72) Inventors: Nathan A. Grenz, Shoreview, MN (US); Ryan Lahm, Lino Lakes, MN (US); Eric Schilling, Ham Lake, MN (US); Brian Schousek, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/703,341

(22) Filed: May 4, 2015

(65) Prior Publication Data
US 2016/0045732 A1 Feb. 18, 2016

Related U.S. Application Data

(60) Provisional application No. 62/037,689, filed on Aug. 15, 2014.

(51) Int. Cl.
*A61N 1/00* (2006.01)
*A61N 1/368* (2006.01)
(Continued)

(52) U.S. Cl.
CPC .............. *A61N 1/368* (2013.01); *A61B 6/466* (2013.01); *A61B 6/504* (2013.01); *A61B 6/5229* (2013.01); *A61N 1/3684* (2013.01); *A61N 1/3686* (2013.01); *A61N 1/36514* (2013.01); *A61N 1/36185* (2013.01)

(58) Field of Classification Search
CPC .. A61N 1/368; A61N 1/36514; A61N 1/3684; A61N 1/3686; A61B 6/466; A61B 6/504; A61B 6/5229
See application file for complete search history.

(56) References Cited

U.S. PATENT DOCUMENTS 4,233,987 A 11/1980 Feingold
4,428,378 A 1/1984 Anderson et al.
(Continued)

FOREIGN PATENT DOCUMENTS

EP 2016976 A1 1/2009
EP 2391270 A1 7/2011
(Continued)

OTHER PUBLICATIONS (PCT/US2015/045222) PCT Notification of Transmittal of the International Search Report and the Written Opinion of the International Searching Authority, mailed Nov. 4, 2015, 10 pages.
(Continued)

*Primary Examiner* — Scott Getzow
(74) *Attorney, Agent, or Firm* — Carol F. Barry

(57) ABSTRACT

Systems, methods, and interfaces are described herein for assisting in a user in configuring cardiac therapy. A projection of a phrenic nerve stimulation map may be projected on a graphical depiction of a portion of a patient's heart. The phrenic nerve stimulation map may indicate to a user the regions of the patient's heart that may have a likelihood of stimulating the patient's phrenic nerve.

41 Claims, 19 Drawing Sheets

(51) Int. Cl.
*A61N 1/365* (2006.01)
*A61B 6/00* (2006.01)
*A61N 1/36* (2006.01)

(56) References Cited

U.S. PATENT DOCUMENTS

| | | | |
|---|---|---|---|
| 4,497,326 A | 2/1985 | Curry | |
| 4,674,511 A | 6/1987 | Cartmell | |
| 5,052,388 A | 10/1991 | Sivula et al. | |
| 5,054,496 A | 10/1991 | Wen et al. | |
| 5,311,873 A | 5/1994 | Savard et al. | |
| 5,443,492 A | 8/1995 | Stokes et al. | |
| 5,628,778 A | 5/1997 | Kruse et al. | |
| 5,671,752 A | 9/1997 | Sinderby et al. | |
| 5,922,014 A | 7/1999 | Warman et al. | |
| 6,055,448 A | 4/2000 | Anderson et al. | |
| 6,187,032 B1 | 2/2001 | Ohyu et al. | |
| 6,236,883 B1 | 5/2001 | Ciaccio et al. | |
| 6,381,493 B1 | 4/2002 | Stadler et al. | |
| 6,393,316 B1 | 5/2002 | Gillberg et al. | |
| 6,473,638 B2 | 10/2002 | Ferek-Petric | |
| 6,507,756 B1 | 1/2003 | Heynen et al. | |
| 6,584,343 B1 | 6/2003 | Ransbury et al. | |
| 6,640,136 B1 | 10/2003 | Helland et al. | |
| 6,772,004 B2 | 8/2004 | Rudy | |
| 6,804,555 B2 | 10/2004 | Warkentin | |
| 6,856,830 B2 | 2/2005 | He | |
| 6,968,237 B2 | 11/2005 | Doan et al. | |
| 6,975,900 B2 | 12/2005 | Rudy et al. | |
| 6,978,184 B1 | 12/2005 | Marcus et al. | |
| 6,980,675 B2 | 12/2005 | Evron et al. | |
| 7,016,719 B2 | 3/2006 | Rudy et al. | |
| 7,031,777 B2 | 4/2006 | Hine et al. | |
| 7,092,759 B2 | 8/2006 | Nehls et al. | |
| 7,142,922 B2 | 11/2006 | Spinelli et al. | |
| 7,215,998 B2 | 5/2007 | Wesselink et al. | |
| 7,286,866 B2 | 10/2007 | Okerlund et al. | |
| 7,308,297 B2 | 12/2007 | Reddy et al. | |
| 7,308,299 B2 | 12/2007 | Burrell et al. | |
| 7,313,444 B2 | 12/2007 | Pianca et al. | |
| 7,321,677 B2 | 1/2008 | Evron et al. | |
| 7,346,381 B2 | 3/2008 | Okerlund et al. | |
| 7,454,248 B2 | 11/2008 | Burrell et al. | |
| 7,499,743 B2 | 3/2009 | Vass et al. | |
| 7,509,170 B2 | 3/2009 | Zhang et al. | |
| 7,565,190 B2 | 7/2009 | Okerlund et al. | |
| 7,587,074 B2 | 9/2009 | Zarkh et al. | |
| 7,599,730 B2 | 10/2009 | Hunter et al. | |
| 7,610,088 B2 | 10/2009 | Chinchoy | |
| 7,613,500 B2 | 11/2009 | Vass et al. | |
| 7,664,550 B2 | 2/2010 | Eick et al. | |
| 7,684,863 B2 | 3/2010 | Parikh et al. | |
| 7,742,629 B2 | 6/2010 | Zarkh et al. | |
| 7,747,047 B2 | 6/2010 | Okerlund et al. | |
| 7,751,882 B1 | 7/2010 | Helland et al. | |
| 7,769,451 B2 | 8/2010 | Yang et al. | |
| 7,778,685 B2 | 8/2010 | Evron et al. | |
| 7,778,686 B2 | 8/2010 | Vass et al. | |
| 7,813,785 B2 | 10/2010 | Okerlund et al. | |
| 7,818,040 B2 | 10/2010 | Spear et al. | |
| 7,848,807 B2 | 12/2010 | Wang | |
| 7,860,580 B2 | 12/2010 | Falk et al. | |
| 7,912,544 B1 | 3/2011 | Min et al. | |
| 7,917,214 B1 | 3/2011 | Gill et al. | |
| 7,941,213 B2 | 5/2011 | Markowitz et al. | |
| 7,953,475 B2 | 5/2011 | Harlev et al. | |
| 7,953,482 B2 | 5/2011 | Hess | |
| 7,983,743 B2 | 7/2011 | Rudy et al. | |
| 7,996,063 B2 | 8/2011 | Vass et al. | |
| 8,019,409 B2 | 9/2011 | Rosenberg et al. | |
| 8,032,229 B2 | 10/2011 | Gerber et al. | |
| 8,036,743 B2 | 10/2011 | Savage et al. | |
| 8,060,185 B2 | 11/2011 | Hunter et al. | |
| 8,150,513 B2 | 4/2012 | Chinchoy | |
| 8,160,700 B1 | 4/2012 | Ryu et al. | |
| 8,180,428 B2 | 5/2012 | Kaiser et al. | |
| 8,195,292 B2 | 6/2012 | Rosenberg et al. | |
| 8,214,041 B2 | 7/2012 | Van Gelder et al. | |
| 8,265,738 B1 | 9/2012 | Min et al. | |
| 8,285,377 B2 | 10/2012 | Rosenberg et al. | |
| 8,295,943 B2 | 10/2012 | Eggen et al. | |
| 8,326,419 B2 | 12/2012 | Rosenberg et al. | |
| 8,401,616 B2 | 3/2013 | Verard et al. | |
| 8,527,051 B1 | 9/2013 | Hedberg et al. | |
| 8,583,230 B2 | 11/2013 | Ryu et al. | |
| 8,617,082 B2 | 12/2013 | Zhang et al. | |
| 8,694,099 B2 | 4/2014 | Ghosh et al. | |
| 8,738,132 B1 | 5/2014 | Ghosh et al. | |
| 8,744,576 B2 | 6/2014 | Munsterman et al. | |
| 2002/0161307 A1 | 10/2002 | Yu et al. | |
| 2004/0097806 A1 | 5/2004 | Hunter et al. | |
| 2004/0172078 A1 | 9/2004 | Chinchoy | |
| 2004/0172079 A1 | 9/2004 | Chinchoy | |
| 2004/0220635 A1 | 11/2004 | Burnes | |
| 2005/0008210 A1 | 1/2005 | Evron et al. | |
| 2005/0027320 A1 | 2/2005 | Nehls et al. | |
| 2005/0096522 A1 | 5/2005 | Reddy et al. | |
| 2005/0149138 A1 | 7/2005 | Min et al. | |
| 2006/0074285 A1 | 4/2006 | Zarkh et al. | |
| 2006/0224198 A1 | 10/2006 | Dong et al. | |
| 2006/0253162 A1 | 11/2006 | Zhang et al. | |
| 2008/0021336 A1 | 1/2008 | Dobak et al. | |
| 2008/0242976 A1 | 10/2008 | Robertson et al. | |
| 2008/0269818 A1 | 10/2008 | Sullivan et al. | |
| 2008/0281195 A1 | 11/2008 | Heimdal | |
| 2008/0306567 A1 | 12/2008 | Park et al. | |
| 2009/0005832 A1 | 1/2009 | Zhu et al. | |
| 2009/0036947 A1 | 2/2009 | Westlund et al. | |
| 2009/0053102 A2 | 2/2009 | Rudy et al. | |
| 2009/0054941 A1 | 2/2009 | Eggen et al. | |
| 2009/0054946 A1 | 2/2009 | Sommer et al. | |
| 2009/0084382 A1 | 4/2009 | Jalde et al. | |
| 2009/0093857 A1 | 4/2009 | Markowitz et al. | |
| 2009/0099619 A1 | 4/2009 | Lessmeier et al. | |
| 2009/0157136 A1 | 6/2009 | Yang et al. | |
| 2009/0198298 A1 | 8/2009 | Kaiser et al. | |
| 2009/0216112 A1 | 8/2009 | Assis et al. | |
| 2009/0232448 A1 | 9/2009 | Barmash et al. | |
| 2009/0254140 A1 | 10/2009 | Rosenberg et al. | |
| 2009/0270729 A1 | 10/2009 | Corbucci et al. | |
| 2009/0270937 A1 | 10/2009 | Yonce et al. | |
| 2009/0299201 A1 | 12/2009 | Gunderson | |
| 2009/0306732 A1 | 12/2009 | Rosenberg et al. | |
| 2009/0318995 A1 | 12/2009 | Keel et al. | |
| 2010/0022873 A1 | 1/2010 | Hunter et al. | |
| 2010/0049063 A1 | 2/2010 | Dobak, III | |
| 2010/0069987 A1 | 3/2010 | Min et al. | |
| 2010/0114229 A1 | 5/2010 | Chinchoy | |
| 2010/0198292 A1 | 8/2010 | Honeck et al. | |
| 2010/0228138 A1 | 9/2010 | Chen | |
| 2010/0268059 A1 | 10/2010 | Ryu et al. | |
| 2011/0004264 A1 | 1/2011 | Siejko et al. | |
| 2011/0022112 A1 | 1/2011 | Min | |
| 2011/0054286 A1 | 3/2011 | Crosby | |
| 2011/0054559 A1* | 3/2011 | Rosenberg | A61N 1/3627 607/28 |
| 2011/0054560 A1 | 3/2011 | Rosenberg et al. | |
| 2011/0112398 A1 | 5/2011 | Zarkh et al. | |
| 2011/0118803 A1 | 5/2011 | Hou et al. | |
| 2011/0137369 A1 | 6/2011 | Ryu et al. | |
| 2011/0144510 A1 | 6/2011 | Ryu et al. | |
| 2011/0190615 A1 | 8/2011 | Phillips et al. | |
| 2011/0201915 A1 | 8/2011 | Gogin et al. | |
| 2011/0213260 A1 | 9/2011 | Keel et al. | |
| 2012/0004567 A1 | 1/2012 | Eberle et al. | |
| 2012/0101543 A1 | 4/2012 | Demmer et al. | |
| 2012/0101546 A1 | 4/2012 | Stadler et al. | |
| 2012/0283587 A1 | 11/2012 | Gosh et al. | |
| 2012/0284003 A1 | 11/2012 | Gosh et al. | |
| 2012/0296387 A1 | 11/2012 | Zhang et al. | |
| 2012/0296388 A1 | 11/2012 | Zhang et al. | |
| 2012/0310297 A1 | 12/2012 | Sweeney | |
| 2012/0330179 A1 | 12/2012 | Yuk et al. | |
| 2013/0006332 A1 | 1/2013 | Sommer et al. | |

(56) References Cited

U.S. PATENT DOCUMENTS

| | | |
|---|---|---|
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0116739 A1 | 5/2013 | Brada et al. |
| 2013/0165988 A1 | 6/2013 | Ghosh |
| 2013/0261688 A1 | 10/2013 | Dong et al. |
| 2013/0289640 A1 | 10/2013 | Zhang et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0236252 A1 | 8/2014 | Ghosh et al. |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032172 A1 | 1/2015 | Ghosh |
| 2015/0032173 A1 | 1/2015 | Ghosh |

FOREIGN PATENT DOCUMENTS

| | | |
|---|---|---|
| EP | 2436309 A2 | 4/2012 |
| WO | WO 98/26712 A1 | 6/1998 |
| WO | WO 00/45700 A1 | 8/2000 |
| WO | WO 01/67950 A1 | 9/2001 |
| WO | 2005039690 A1 | 5/2005 |
| WO | WO 2005/056108 A2 | 6/2005 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/013994 A3 | 4/2007 |
| WO | WO 2007/139456 A1 | 12/2007 |
| WO | WO 2008/151077 A2 | 12/2008 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2011/070166 A1 | 6/2011 |
| WO | WO 2011/090622 A1 | 7/2011 |
| WO | WO 2012/037471 A2 | 3/2012 |
| WO | WO 2012/037471 A3 | 6/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |

OTHER PUBLICATIONS

U.S. Appl. No. 14/173,288, filed Feb. 5, 2014, Sambelashvili.
U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.
International Search Report and Written Opinion issued May 3, 2012 for International Application No. PCT/US2014/036262; 9 pages
International Search Report and Written Opinion issued May 3, 2012 for International Application No. PCT/US2014/036302; 9 pages.
International Search Report and Written Opinion issued Aug. 6, 2014 for International Application No. PCT/US2014/036153; 14 pages.
International Search Report and Written Opinion issued Nov. 7, 2014 for International Application No. PCT/US2014/036163; 12 pages.
International Search Report and Written Opinion issued Oct. 28, 2014 for International Application No. PCT/US2014/041928; 15 pages.
International Search Report and Written Opinion issued Oct. 24, 2014 for International Application No. PCT/US2014/041929; 14 pages.
International Search Report and Written Opinion issued on Mar. 9, 2015 for International Application No. PCT/US2014/069214; 11 pages.
International Search Report and Written Opinion issued on Mar. 17, 2015, for International Application No. PCT/US2014/069192; 11 pages.
International Search Report and Written Opinion issued on Mar. 16, 2015 for International Application No. PCT/US2014/069182; 11 pages.
International Search Report and Written Opinion issued on Apr. 8, 2015 for International Application No. PCT/US2014/069070; 11 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
"CardioGuide System Enables Real-Time Navigation of Left Ventricular Leads During Medtronic CRT Implants," Press Release, Apr. 9, 2013, Medtronic, Inc., 2 pgs.
Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.

(56) References Cited

OTHER PUBLICATIONS

Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of ST Segment Changes in Acute Myocardial Infarction," *Circulation*, 1993; 87: 773-782.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

Ridgeway, "The State of Boosting," *Computing Science and Statistics*, 1999; 31:172-181.

Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-222.

Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Sperzel et al., "Intraoperative Characterization of Interventricular Mechanical Dyssynchrony Using Electroanatomic Mapping System—A feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms : a simulation study," Circulation Research, 1989, 64:449-462.

Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-634.

Turner et al, "Electrical and Mechanical Components of Dyssynchrony in Heart Failure Patients with Normal QRS Duration and Left Bundle-Branch Block," *Circulation* 2004; 109: 2544-2549.

van Deursen et al., "Vectorcardiography as a Tool for Easy Optimization of Cardiac Resynchronization Therapy in Canine Left Bundle Branch Block Hearts," *Circulation Arrhythmia and Electrophysiology*, Jun. 1, 2012; 5(3):544-552.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

* cited by examiner

SYSTEMS, METHODS, AND INTERFACES FOR CONFIGURING CARDIAC THERAPY

This application claims the benefit of U.S. Provisional Patent Application 62/037,689 entitled "Systems, Methods, and Interfaces for Configuring Cardiac Therapy" and filed on Aug. 15, 2014, which is incorporated herein by reference in its entirety.

The disclosure herein relates to systems, methods, and interfaces for assisting a user in configuring cardiac therapy. More specifically, systems, methods, and interfaces may assist a user in the selection of a pacing location.

Cardiac pacing electrodes may be used in various systems, apparatus, and methods for medical treatment of a patient. Cardiac pacing electrodes may be located adjacent, or in contact, with tissue (e.g., cardiac tissue, skin, etc.) of a patient to deliver cardiac pacing therapy to the patient using various different electrical pacing vectors. Some electrodes and/or electrical pacing vectors used for cardiac pacing therapy may inadvertently or unintentionally stimulate the patient's phrenic nerve, e.g., causing undesired diaphragm movement, patient discomfort, etc.

Phrenic nerve stimulation detection has been disclosed in U.S. Pat. App. Pub. No. 2012/0296388 A1 filed on May 17, 2012 and entitled "PHRENIC NERVE STIMULATION DETECTION USING HEART SOUNDS" and U.S. Pat. App. Pub. No. 2012/0296387 A1 filed on Nov. 22, 2012 and entitled "PHRENIC NERVE STIMULATION DETECTION USING HEART SOUNDS," each of which is incorporated herein by reference in its entirety.

SUMMARY

The exemplary systems, methods, and interfaces described herein may be configured to provide assistance to a user (e.g., a physician) in configuring cardiac therapy (e.g., location selection of pacing therapy, etc.). The systems, methods, and interfaces may be described as being noninvasive. For example, the systems, methods, and interfaces may not need, or include, implantable devices such as leads, probes, sensors, catheters, etc. to evaluate cardiac therapy. Instead, the systems, methods, and interfaces may use imaging apparatus located outside of the patient's body.

The exemplary systems, methods, and interfaces may use a phrenic nerve stimulation map. The phrenic nerve stimulation map may include phrenic nerve stimulation information (e.g., data) for a plurality of areas, each of the areas corresponding to different region of a heart (e.g., different regions of a patient's left ventricle). The phrenic nerve stimulation information for an area of the map may include data regarding the likelihood of phrenic nerve stimulation if pacing therapy was delivered proximate the corresponding region of the heart.

The phrenic nerve stimulation map may be projected onto a graphical representation of a patient's heart, e.g., that is generated based on images of the patient's heart. To project the phrenic nerve stimulation map on the graphical representation of a patient's heart, features may be detected within the images of the patient's heart from which the spatial geometry of the regions (e.g., regions or portions of the patient's left ventricle) of the patient's heart may be determined. The phrenic nerve stimulation map may then be projected about, or related to, a graphical representation of the patient's heart (e.g., a portion of blood vessel anatomy proximate the patient's left ventricle) based on the detected features and/or spatial geometry. Additionally, the graphical representations of the patient's heart with the phrenic nerve stimulation map may assist a user to, e.g., navigate a lead including one or more pacing electrodes to one or more pacing locations within or proximate the patient's heart, select one or more pacing vectors to be used for pacing therapy, etc.

One exemplary system for assisting a user in configuring cardiac therapy may include a display apparatus and a computing apparatus coupled to display apparatus. The display apparatus may include a graphical user interface configured to depict at least a portion of the patient's heart. The computing apparatus may be configured to provide the graphical user interface displayed on the display apparatus to assist a user in selecting a pacing location. Further, the computing apparatus may be further configured to provide a phrenic nerve stimulation map including a plurality of areas (e.g., 17 or less areas) corresponding to different regions of a human heart (e.g., corresponding to different regions of the left ventricle of the human heart). Each area of the plurality of areas may be configured to provide phrenic nerve stimulation information for the corresponding region of the human heart. Further, the computing apparatus may be further configured to detect one or more features of the patient's heart (e.g., an epicardial border, the middle cardiac vein, the anterior interventricular vein, the interventricular septum, the coronary sinus of the patient's heart etc.) within one or more images of the patient's heart, project the phrenic nerve stimulation map on a graphical representation of at least a portion of the patient's heart (e.g., at least a portion of the blood vessel anatomy of the patient's heart) based on the one or more detected features of the patient's heart, and display, on the graphical user interface, the graphical representation of at least a portion of the patient's heart and the projected phrenic nerve stimulation map.

One exemplary method for assisting a user in configuring cardiac therapy may include providing a phrenic nerve stimulation map. The phrenic nerve stimulation map may include a plurality of areas (e.g., 17 or less areas) corresponding to different regions of a human heart (e.g., corresponding to different regions of the left ventricle of the human heart), and each area of the plurality of areas is configured to provide phrenic nerve stimulation information for the corresponding region of the human heart. The exemplary method may further include detecting one or more features of the patient's heart (e.g., an epicardial border, the middle cardiac vein, the anterior interventricular vein, the interventricular septum, the coronary sinus of the patient's heart etc.) within one or more images of the patient's heart, projecting the phrenic nerve stimulation map on a graphical representation of at least a portion of the patient's heart (e.g., at least a portion of the blood vessel anatomy of the patient's heart) based on the one or more detected features of the patient's heart, and displaying, on a graphical user interface, the graphical representation of at least a portion of the patient's heart and the projected phrenic nerve stimulation map.

One exemplary system for assisting a user in configuring cardiac therapy may include display means for depicting, on a graphical user interface, at least a portion of the patient's heart; computing means for providing the graphical user interface displayed on the display means to assist a user in selecting a pacing location. The computing means may be further for providing a phrenic nerve stimulation map including a plurality of areas (e.g., 17 or less areas) corresponding to different regions of a human heart (e.g., corresponding to different regions of the left ventricle of the human heart), where each area of the plurality of areas is configured to provide phrenic nerve stimulation information for the corresponding region of the human heart. The computing means may be further for detecting one or more features of the patient's heart (e.g., an epicardial border, the middle cardiac vein, the anterior interventricular vein, the interventricular septum, the coronary sinus of the patient's heart etc.) within one or more images of the patient's heart, projecting the phrenic nerve stimulation map on a graphical representation of at least a portion of the patient's heart (e.g., at least a portion of the blood vessel anatomy of the patient's heart) based on the one or more detected features of the patient's heart, and displaying, on a graphical user interface, the graphical representation of at least a portion of the patient's heart and the projected phrenic nerve stimulation map.

In one or more embodiments, projecting the phrenic nerve stimulation map on the graphical representation of at least a portion of the patient's heart based on the one or more detected features of the patient's heart may include defining a plane curve based on a plurality of points identified in the one or more detected features of the patient's heart. Further, the plurality of points identified in the detected one or more features of the patient's heart may include one or more of a point proximate an intersection between the middle cardiac vein and the coronary sinus of the patient's heart, a point along the middle cardiac vein, a point proximate a distal end of the anterior interventricular vein of the patient's heart, a point along the anterior interventricular vein of the patient's heart, a point proximate the apex of the patient's heart, and a point proximate the septal groove of the patient's heart.

In one or more embodiments, the phrenic nerve stimulation information of the plurality of areas of the phrenic nerve stimulation map may include an indication of likelihood of phrenic nerve stimulation (e.g., a high indication of phrenic nerve stimulation, a medium indication of phrenic nerve stimulation, and a low indication of phrenic nerve stimulation, etc.) in response to pacing therapy delivered to the corresponding region of the human heart. In at least one embodiment, the plurality of areas of the phrenic nerve stimulation map may be color-coded to provide an indication of likelihood of phrenic nerve stimulation in response to pacing therapy delivered to the corresponding regions of the human heart.

In one or more embodiments, imaging apparatus may be configured to image the patient's heart, and the graphical representation of at least a portion of the patient's heart is generated based on the one or more images. Further, at least one image of the one or more images of the patient's heart may be displayed proximate the graphical representation of at least a portion of the patient's heart and the projected phrenic nerve stimulation map. In at least one embodiment, the graphical representation of at least a portion of the patient's heart and the projected phrenic nerve stimulation map may overlay the displayed at least one image of the one or more images of the patient's heart.

In one or more embodiments, the graphical representation of at least a portion of the patient's heart may be generated based on the one or more images of the patient's heart. Further, the graphical representation of at least a portion of the patient's heart and the projected phrenic nerve stimulation map displayed on the graphical user interface may be a three-dimensional graphical representation.

In one or more embodiments, a user may be allowed to update the phrenic nerve stimulation information in an area of the plurality of areas of the phrenic nerve stimulation map and the graphical representation of at least a portion of the patient's heart and the projected phrenic nerve stimulation map including the updated phrenic nerve stimulation information may be displayed on the graphical user interface.

In one or more embodiments, phrenic nerve stimulation may be detected at a pacing location, the phrenic nerve stimulation information may be updated in an area of the plurality of areas of the phrenic nerve stimulation map corresponding to the pacing location, and the graphical representation of at least a portion of the patient's heart and the projected phrenic nerve stimulation map including the updated phrenic nerve stimulation information may be displayed on the graphical user interface.

One exemplary system for assisting a user in configuring cardiac therapy may include a display apparatus and computing apparatus coupled to display apparatus. The display apparatus may include a graphical user interface configured to depict at least a portion of the patient's heart. The computing apparatus may be configured to provide the graphical user interface displayed on the display apparatus to assist a user in selecting a pacing location. The computing apparatus may be further configured to provide an information map (e.g., one or more of a phrenic nerve stimulation map, a scar risk map, a dyssynchrony map, an electrical timing map, a tissue viability map, a neighboring medical device map, a contractility map, a tissue strain map, etc.). The information map may include a plurality of areas corresponding to different regions of a human heart and each area of the plurality of areas may be configured to provide information for the corresponding region of the human heart. The computing apparatus may be further configured to detect one or more features of the patient's heart within one or more images of the patient's heart, project the information map on a graphical representation of at least a portion of the patient's heart based on the one or more detected features of the patient's heart, and display, on the graphical user interface, the graphical representation of at least a portion of the patient's heart and the projected information map.

One exemplary method for assisting a user in configuring cardiac therapy may include providing an information map (e.g., one or more of a phrenic nerve stimulation map, a scar risk map, a dyssynchrony map, an electrical timing map, a tissue viability map, a neighboring medical device map, a contractility map, a tissue strain map, etc.). The information map may include a plurality of areas corresponding to different regions of a human heart, and each area of the plurality of areas is configured to provide information for the corresponding region of the human heart. The exemplary method may further include detecting one or more features of the patient's heart within one or more images of the patient's heart, projecting the information map on a graphical representation of at least a portion of the patient's heart based on the one or more detected features of the patient's heart, and displaying, on a graphical user interface, the graphical representation of at least a portion of the patient's heart and the projected information map.

One exemplary system for assisting a user in configuring cardiac therapy may include display means for depicting, on a graphical user interface, at least a portion of the patient's heart and computing means for providing the graphical user interface displayed on the display means to assist a user in selecting a pacing location. The computing means may be further for providing an information map (e.g., one or more of a phrenic nerve stimulation map, a scar risk map, a dyssynchrony map, an electrical timing map, a tissue viability map, a neighboring medical device map, a contractility map, a tissue strain map, etc.) including a plurality of areas corresponding to different regions of a human heart, where each area of the plurality of areas is configured to provide information for the corresponding region of the human heart. The computing means may be further for detecting one or more features of the patient's heart within one or more images of the patient's heart, projecting the information map on a graphical representation of at least a portion of the patient's heart based on the one or more detected features of the patient's heart, and displaying, on a graphical user interface, the graphical representation of at least a portion of the patient's heart and the projected information map.

Exemplary systems, methods, and interfaces, describe herein may allow advanced analysis of coronary vein anatomy by generating a three-dimensional (3D) model and supporting electrode tracking for navigation. Users (e.g., physicians) may be able to predict where phrenic nerve stimulation is likely to occur (e.g., intraoperatively, post implant, etc.) using the exemplary systems, methods, and interfaces.

The exemplary systems, methods, and interfaces may be configured to overlay a left ventricle (LV) segment model over fluoroscopic images of the LV and/or other portions of the patient's heart and display the probability of phrenic nerve stimulation thereon or thereabout. More specifically, two or more occlusive venograms may be collected and a 3D model may be created based on the venograms. Within the venograms and/or 3D model, the epicardial border may be detected. Further, the middle cardiac and anterior interventricular vein may be detected and used to define the septum and right ventricular (RV) insertion points in order to segment the LV into 17, 16, or 15 segment models. The segment model may be then overlaid on the 3D model and the probability of phrenic nerve stimulation may be displayed on the model. The probability of phrenic nerve stimulation can be determined from published literature, historical cases, etc. and can be updated (e.g., during the implant procedure, post implant in follow up, etc.) if phrenic nerve stimulation is encountered.

The LV segment model may provide an additional benefit by visualizing the apex of the heart because implanters may want to avoid apical LV lead placement (which may be associated with less desirable cardiac resynchronization therapy outcomes). Further, heart rotation can also mislead, or confuse, implanters about where a lead is actually placed, and the exemplary systems, methods, and interfaces may provide objective, accurate info on where the lead is located.

It may be described that exemplary systems, methods, and interfaces may allow for easy visualization of LV segments. The PNS probability map described herein may be configured to show the likelihood of phrenic nerve stimulation. Further, the exemplary systems, methods, and interfaces may be described as providing accurate segmentation of the heart by accounting for heart rotation. Further, the exemplary systems, methods, and interfaces may provide information to a user for avoidance of apical pacing and phrenic nerve stimulation.

It may be further described that the exemplary systems, methods, and interfaces provide value to users (e.g., implanters) by improving their visualization of the LV and helping to avoid phrenic nerve stimulation. Further, the exemplary systems, methods, and interfaces may improve LV implant procedures and outcomes.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
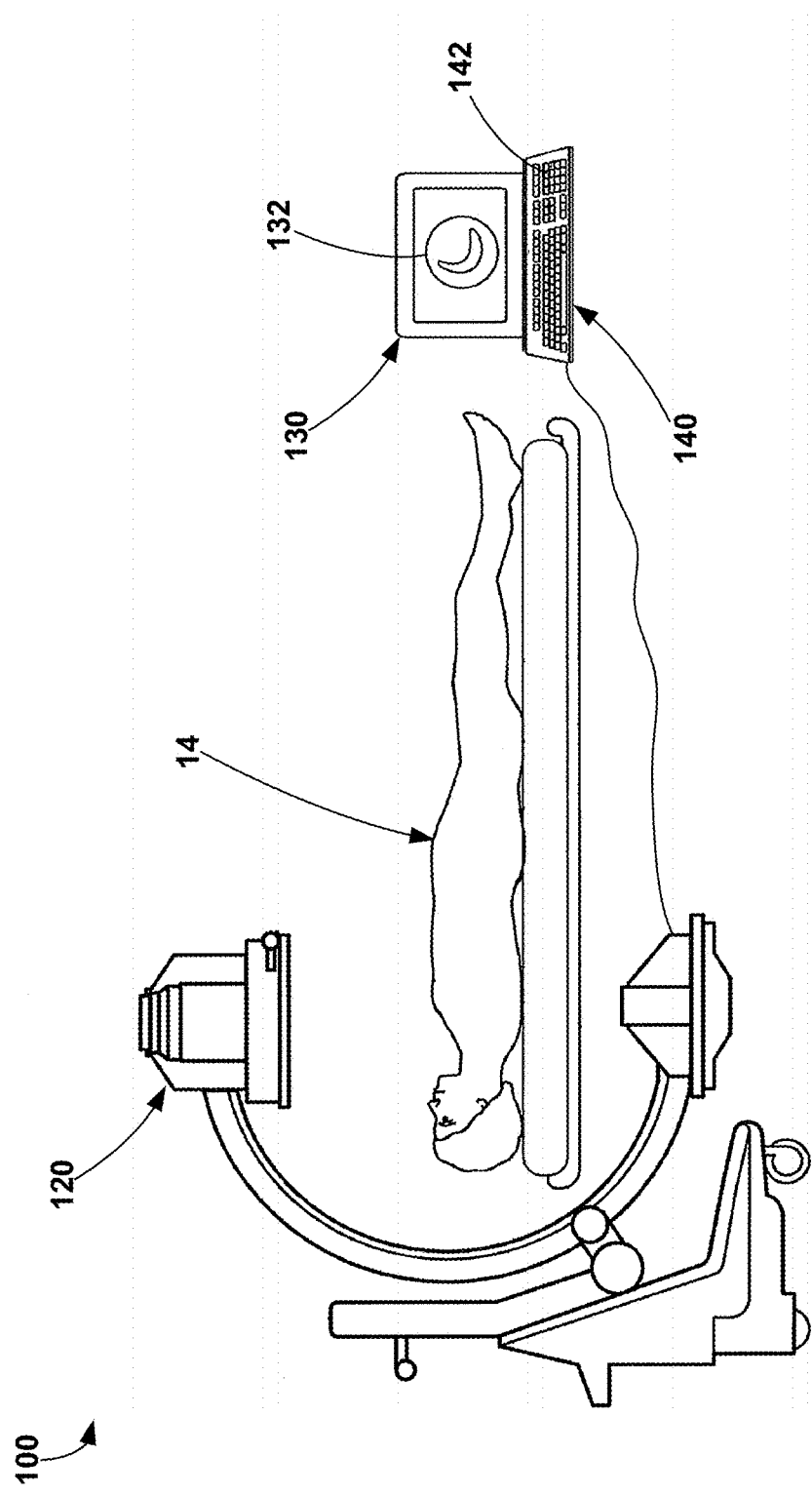
FIG. 1 is a diagram of an exemplary system including imaging apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, apparatus, and methods shall be described with reference to FIGS. 1-15. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

As described herein, various exemplary systems, methods, and interfaces may be configured to use imaging apparatus, display apparatus, and computing apparatus to noninvasively assist a user (e.g., a physician) in configuring cardiac therapy. For example, the exemplary systems, methods, and interfaces may assist a user in the selection of a pacing location (e.g., implantation site regions) proximate a patient's heart for the delivery of cardiac pacing. A user may use the exemplary systems, methods, and interfaces to configure the cardiac pacing vector and/or to navigate implantable electrodes with or proximate to the patient's heart. An exemplary system 100 including imaging apparatus 120, display apparatus 130, and computing apparatus 140 is depicted in FIG. 1.

The imaging apparatus 120 may be any type of imaging apparatus configured to image, or provide images of, at least a portion of the patient in a non-invasive manner. For example, the imaging apparatus 120 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in configuring cardiac therapy by, e.g., assisting the user in selecting a pacing location proximate a patient's heart.

Further, the exemplary systems, methods, and interfaces may provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 120 may be configured to capture, or take, x-ray images (e.g., two-dimensional (2D) x-ray images, three-dimensional 3D) x-ray images, etc.) of the patient 14. The imaging apparatus 120 may be operatively coupled (e.g., through one or wired electrical connections, wirelessly, etc.) to the computing apparatus 140 such that the images captured by the imaging apparatus 120 may be transmitted to the computing apparatus 140. Further, the computing apparatus 140 may be configured to control the imaging apparatus 120 to, e.g., configure the imaging apparatus 120 to capture images, change one or more settings of the imaging apparatus 120, etc.

It will be recognized that while the imaging apparatus 120 as shown in FIG. 1 may be configured to capture x-ray images, any other alternative imaging modality may also be used by the exemplary systems, methods, and interfaces described herein. For example, the imaging apparatus 120 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 120 may be configured to capture a plurality of consecutive images (e.g., continuously) to provide video frame data. In other words, a plurality of images taken over time using the imaging apparatus 120 may provide video frame, or motion picture, data (e.g., real-time video, etc.). Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 130 and the computing apparatus 140 may be configured to display and analyze data such as, e.g., one or more captured images, one or more graphical representations based on captured images, one or more data sets indicative of phrenic nerve simulation, one or more data sets indicative of scar risk, one or more data sets indicative of dyssynchrony, etc. to noninvasively assist a user in selecting a pacing location. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in location selection of an implantable electrode, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 to view and/or select one or more target or candidate locations of a portion of a patient's heart as further described herein.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including graphical depictions of anatomy of a patient's heart, images of a patient's heart, graphical depictions of locations of one or more electrodes, graphical depictions of one or more data sets such as a phrenic nerve stimulation map, a scar risk map, a dyssynchrony map, alphanumeric representations of one or more values, graphical depictions or actual images of implanted electrodes and/or leads, etc. For example, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, image projection algorithms, image overlaying algorithms, feature recognition algorithms, or any other processing required to implement one or more exemplary methods and/or processes described herein. Data stored and/or used by the computing apparatus 140 may include, for example, image data from the imaging apparatus 120, data sets (e.g., segmented heart models, phrenic nerve stimulation maps, scar risk maps, dyssynchrony information, electrical timing maps, tissue viability maps, neighboring medical device maps, contractility maps, tissue strain maps, etc.), graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.). The exact configuration of the computing apparatus 130 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The imaging apparatus 120, which may be a computerized tomography X-ray machine, may be directed at the patient's heart and activated to produce a time sequence of X-ray images (e.g., video frame data, real-time video, etc.) of the heart area at the field of view. In order to expose blood vessels (e.g., such as the coronary vessels) at the heart area under view, the X-ray images may be preferably obtained under angiography procedure by injecting contrast agent to the patient. Where the vessels to be detected are the coronary veins, the angiography may be carried out after a balloon is inserted and inflated inside the vein, e. g., the coronary sinus, so as to prevent blood flow from dispersing the contrast agent before the images are taken.

For example, a time sequence of two-dimensional X-ray projection images may be captured by imaging apparatus of FIG. 1 and stored by the computing apparatus 140. The two-dimensional images may be angiograms (e.g., venograms) taken after the patient has been injected with contrast agent. The time sequence may include "snapshots" (e.g., angiographic cine-runs) of the coronary vessel under the same projection angle during at least part of the cardiac cycle of the patient. Further, the projection direction may be selected to be substantially orthogonal to the surface of the heart at the region of interest or to the main velocity component thereof.

Examples of systems and/or imaging apparatus configured to capture images of a patient's heart and/or generate graphical representations of one or more portions of the patient's heart may be described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al.

issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

Figure 2:
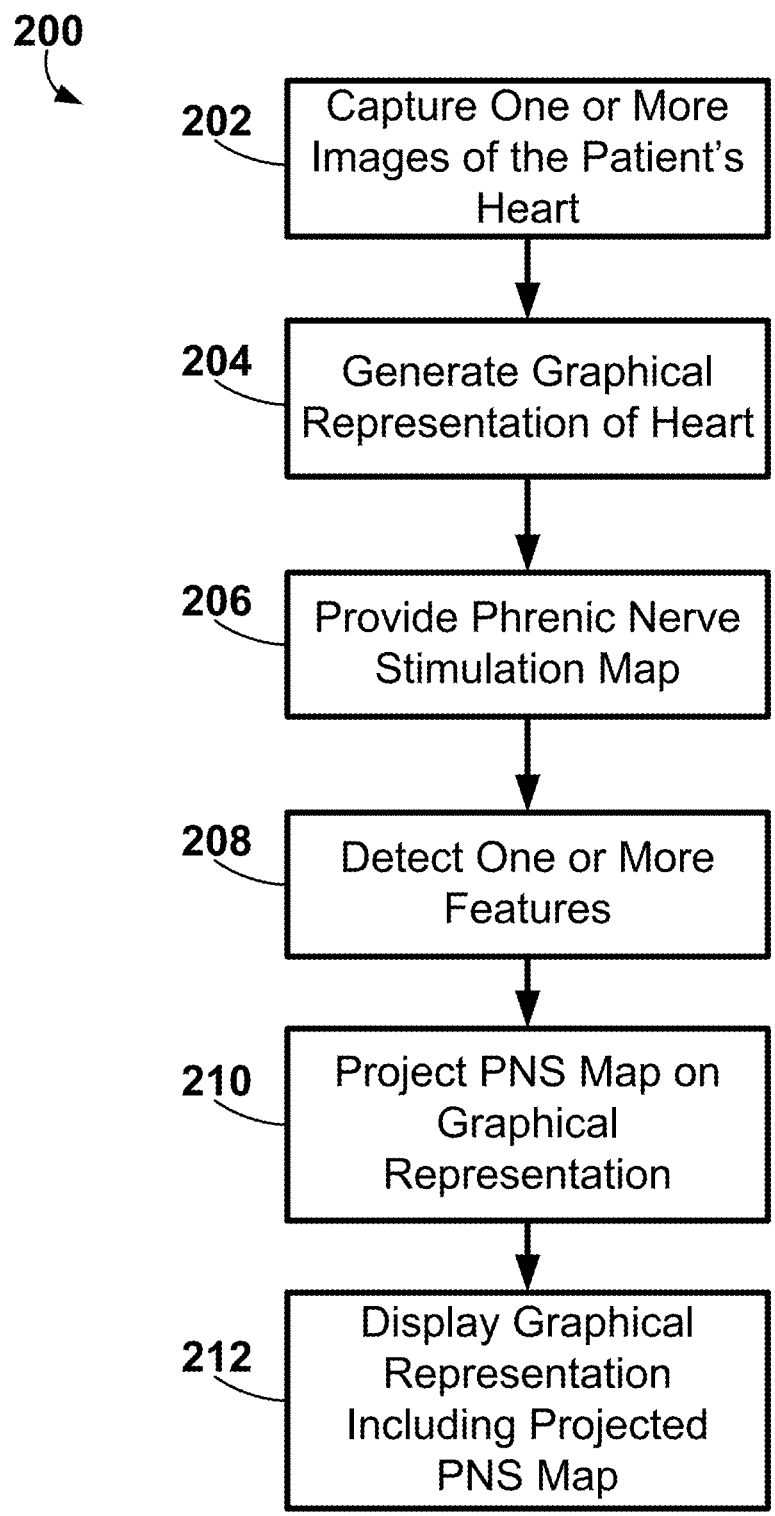
FIG. 2 is a block diagram of an exemplary method of assisting a user in configuring cardiac therapy.

An exemplary method 200 for assisting a user in configuring cardiac therapy is depicted in FIG. 2, which may be executed using the systems, apparatus, and graphical user interfaces described herein. The exemplary method 200 may include capturing one or more images of a patient's heart 202 using, e.g., the imaging apparatus 120 of FIG. 1. In at least one embodiment, two or more images are captured.

Figure 3A:
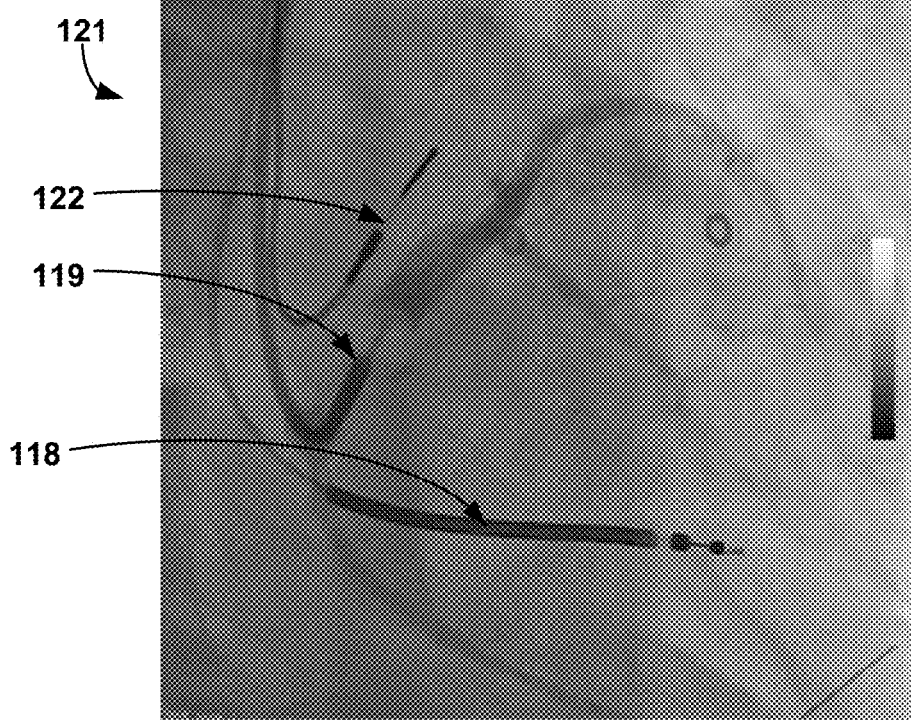
FIG. 3A is an image of a heart.
Figure 3B:
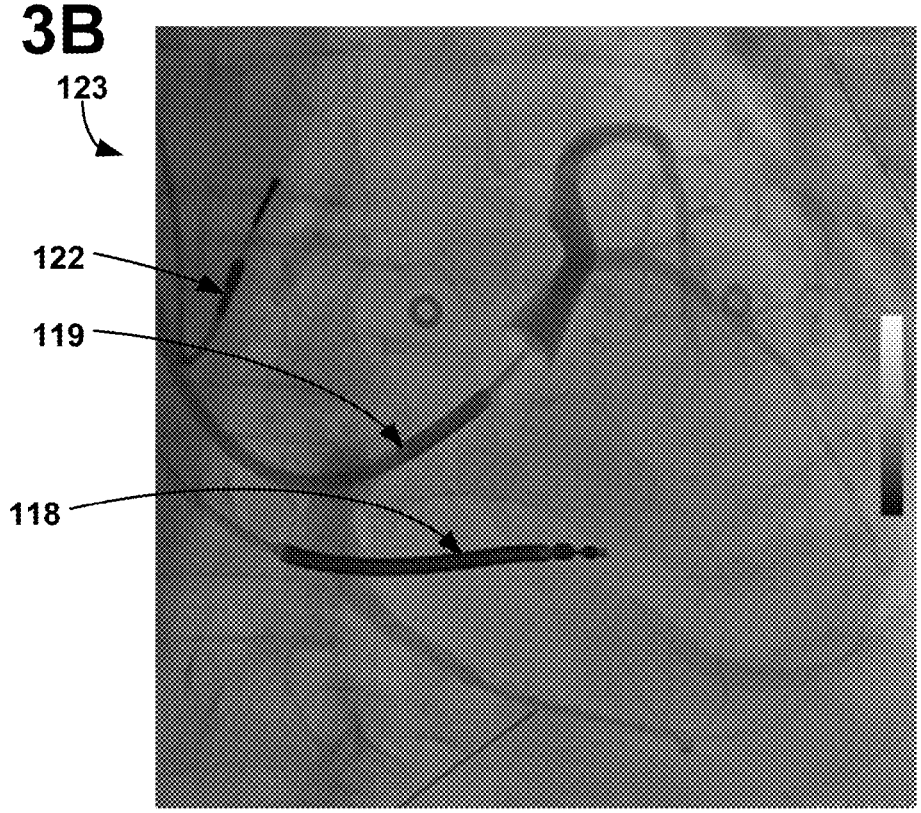
FIG. 3B is another image of the heart of FIG. 3A.

Two exemplary captured images 121, 123 of a patient's heart are depicted in FIGS. 3A-3B, respectively. More specifically, the first image 121 of FIG. 3A shows a right anterior view of the patient's heart and the second image 123 of FIG. 3B shows an anterior-posterior view of the patient's heart. As shown, two leads 118, 122, which may be similar to leads 18, 22 described herein with reference to FIGS. 13-15, and a catheter 119 are also shown in the images 121, 123. The right ventricular (RV) lead 118 extends through one or more veins, the superior vena cava, and the right atrium, and into the right ventricle of the heart. The left ventricular (LV) coronary sinus catheter 119 extends through one or more veins, the vena cava, and the right atrium, and may be configured to assist in the placement of a lead into the coronary sinus to a region adjacent to the free wall of the left ventricle of the heart. The right atrial (RA) lead 122 extends through one or more veins and the vena cava, and into the right atrium of the heart.

Figure 4:
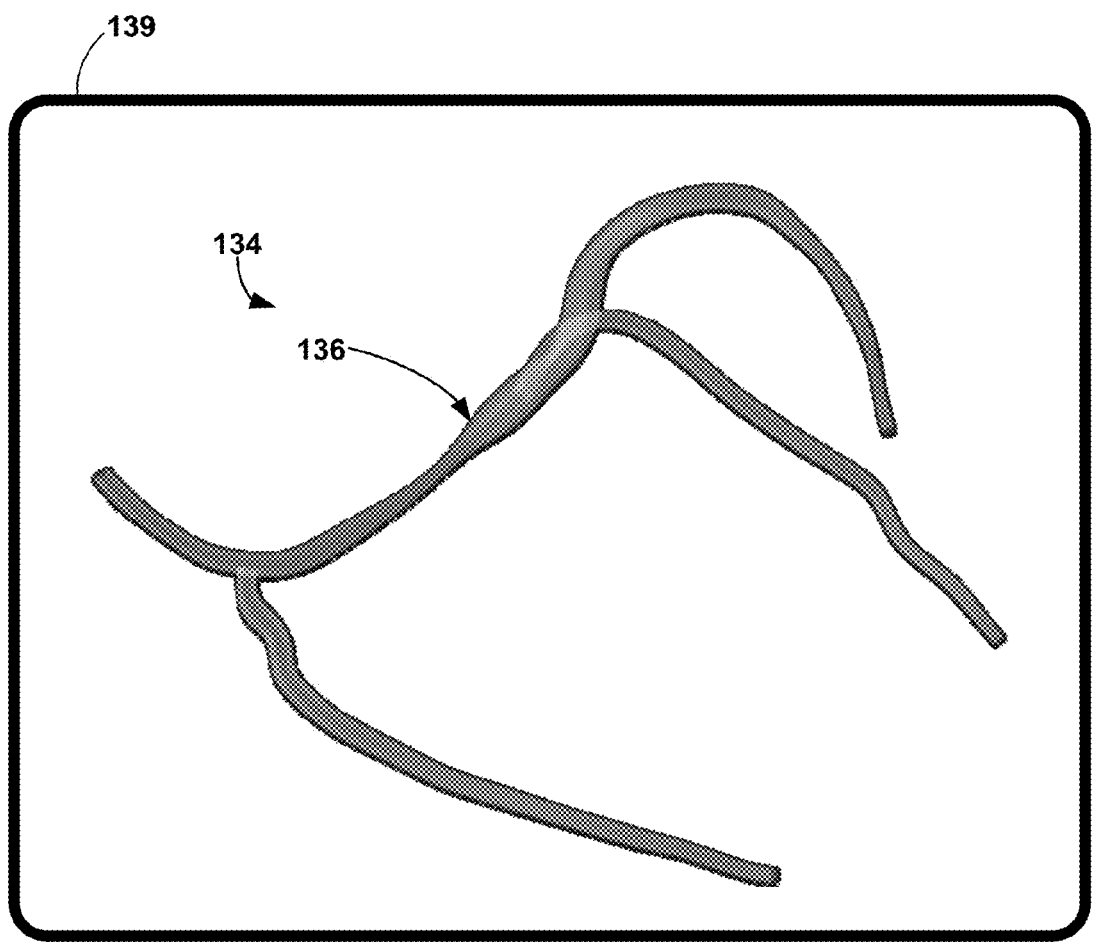
FIG. 4 is a graphical representation of a portion of the blood vessel anatomy of the heart of FIGS. 3A-3B.

The captured images may be used to generate a graphical representation 134 of a least a portion of the patient's heart 204 as shown in FIG. 4. The graphical representation 134 of a least a portion of the patient's heart 204 as shown is a portion of blood vessel anatomy 136 of a patient's heart. More specifically, the blood vessel anatomy 136 includes the coronary sinus located proximate the left ventricle of a patient. The blood vessel anatomy 136 further includes a plurality of branches of the coronary sinus. Each branch, as well as multiple locations within each branch, may provide pacing, or candidate, locations for the delivery of cardiac therapy. As further indicated by the outline around the graphical representation 134 in FIG. 4, the exemplary method 200 may include displaying the generated graphical representation 134 of a least a portion of the patient's heart using a graphical user interface 139 on display apparatus. Although the generated graphical representation 134 of a least a portion of the patient's heart includes blood vessel anatomy 136 of a patient's heart, it is to be understood that any part of a patient's anatomy may be generated and/or displayed.

Figure 5A:
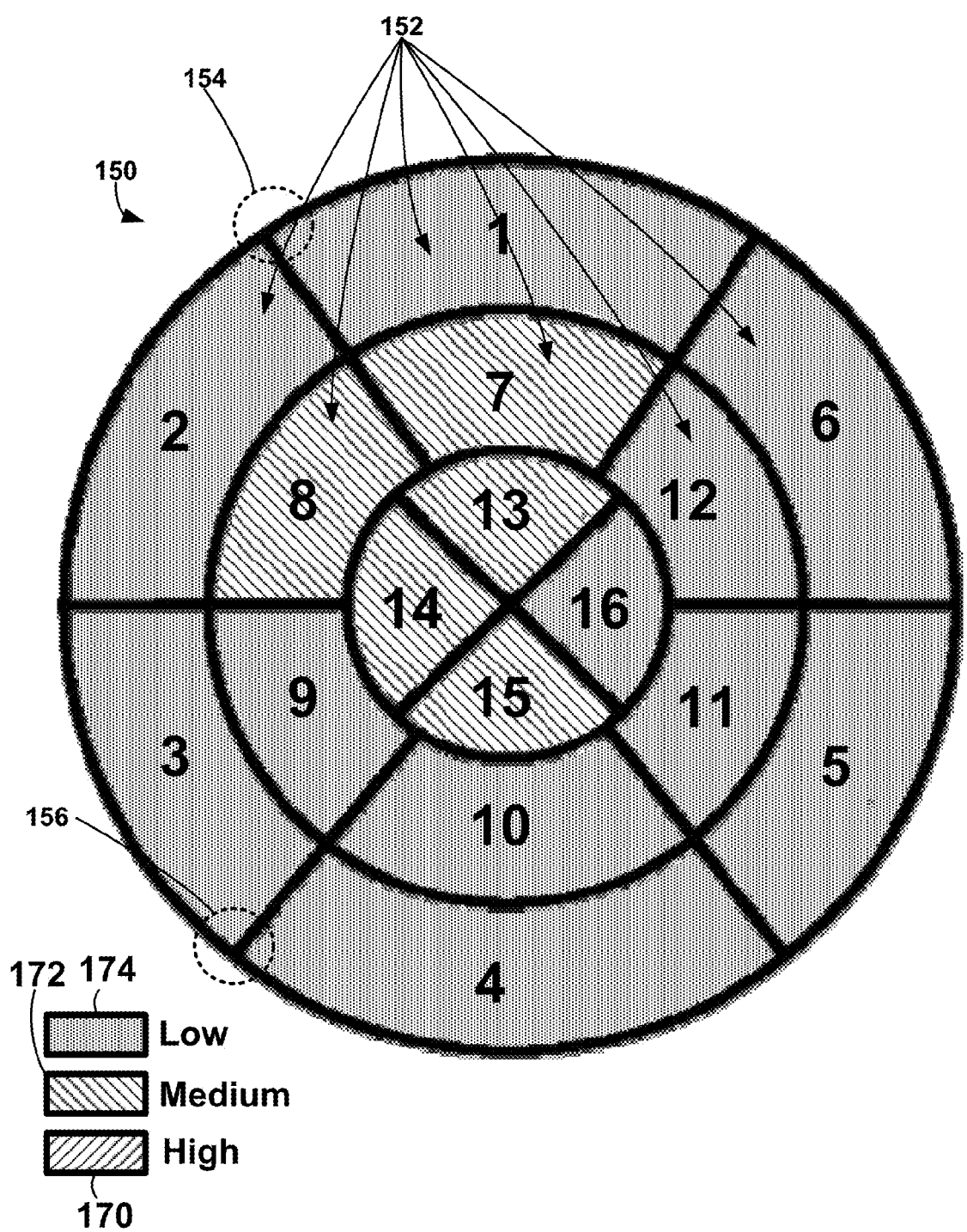
FIG. 5A is an exemplary two-dimensional phrenic nerve stimulation map.
Figure 5B:
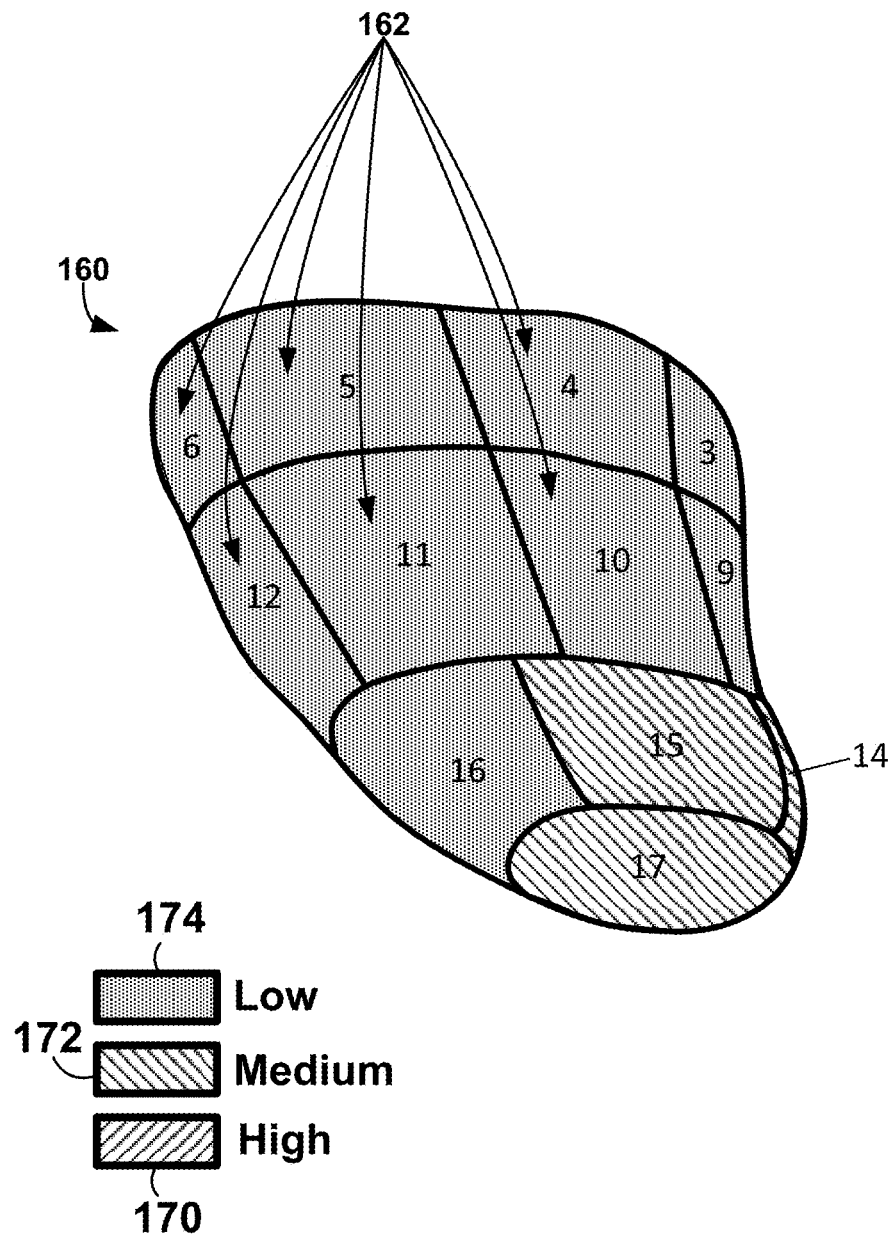
FIG. 5B is an exemplary three-dimensional phrenic nerve stimulation map.

The exemplary method 200 may further include providing a phrenic nerve stimulation map 206. An exemplary two-dimensional (2D) phrenic nerve stimulation map 150 is depicted in FIG. 5A, and an exemplary three-dimensional (3D) phrenic nerve stimulation map 160 is depicted in FIG. 5B. Each of the phrenic nerve stimulation maps 150, 160 may include a plurality of areas 152, 162, respectively, corresponding to different regions of a human heart (e.g., regions of the left ventricle of a human heart). The areas 152 of the map 150 may be numerically labeled 1-16 (which, e.g., correspond to a standard 16 segment model of a human heart and the areas 162 of the map 160 may be numerically labeled 1-17 (which, e.g., correspond to a standard 17 segment model of a human heart, correspond to 17 segments of the left ventricle of a human heart, etc.). Although the exemplary maps 150, 160 depicted herein include 16 and 17 areas respectively, it is to be understood that the phrenic nerve stimulation maps may include more than 17 areas and less than 16 areas. For example, phrenic nerve stimulation maps may include 4 or more areas, 5 or more areas, 7 or more areas, 9 or more areas, 11 or more areas, 15 or more areas, 20 or more areas, 25 or more areas, etc. Further, for example, phrenic nerve stimulation maps may include 50 or less areas, 40 or less areas, 30 or less areas, 27 or less areas, 23 or less areas, 18 or less areas, 13 or less areas, 8 or less areas, etc.

Areas 152, 162 of the maps 150, 160 may include basal anterior area 1, basal anteroseptal area 2, basal inferospetal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. As shown, location 154 may correspond to the anterior interventricular vein of a human heart and location 156 may correspond to the middle cardiac vein of a human heart.

The plurality of areas 152, 162 may be configured to provide phrenic nerve stimulation information for the corresponding regions of the human heart. For example, each area may provide an indication of likelihood of phrenic nerve stimulation in response to cardiac pacing therapy delivered to the corresponding region of the patient's heart. More specifically, each area may provide a high indication 170 of phrenic nerve stimulation, a medium indication 172 of phrenic nerve stimulation, and a low indication 174 of phrenic nerve stimulation. As shown, the indications 170, 172, 174 are shown by different cross-hatching within the areas 152, 162 of the maps 150, 162. Further, the indications 170, 172, 174 may be shown by color-coding the phrenic nerve stimulations maps 150, 152.

The phrenic nerve stimulation information may be based on one or more sources. For example, the phrenic nerve stimulation information may include medical studies, historical case databases, patient history, population statistics, patient-specific images/models, etc.

As shown in the maps 150, 160, the basal anterior area 1, basal anteroseptal area 2, basal inferospetal area 3, basal inferior area 4, basal inferolateral area 5, basal anterolateral area 6, mid-inferoseptal area 9, mid-inferior area 10, mid-inferolateral area 11, mid-anterolateral area 12, and apical lateral area 16 each indicate a low likelihood of phrenic nerve stimulation. Further, the mid-anterior area 7, mid-anteroseptal area 8, apical anterior area 13, apical septal area 14, apical inferior area 15, and apex area 17 indicate a medium likelihood of phrenic nerve stimulation.

As described herein, the plurality of areas 152, 162 of the maps 150, 160, respectively, correspond to different regions of a human heart, and as such, the maps may be used to depict the phrenic nerve stimulation proximate, or projected on, the corresponding regions of the heart on a graphical representation of the heart. To provide such functionality, the exemplary method 200 further includes detecting one or more features of the patient's heart within one or more images of the patient's heart 208. The features may be defined as any identifiable points or structures of a patient's heart within the captured one or more images. Some features may readily correspond to regions of the patient's heart. Further, some features, may provide spatial indicators, or flags, representing a part, or point, within a feature of the patient's heart. For example, the one or more features may include one or more points of or the entire anterior interventricular vein (AIV), middle cardiac vein (MCV), the interventricular septum, the coronary sinus (CS), the epicardial border, a coronary vein, venous bifurcations, high curvature structures, objects (e.g., leads, electrodes, devices, etc.) located in the heart, etc. Further, one or more points may be identified such as, e.g., a point proximate an intersection between the middle cardiac vein and the coronary sinus of the patient's heart, a point along the middle cardiac vein, a point proximate a distal end of the anterior interventricular vein of the patient's heart, a point along the anterior interventricular vein of the patient's heart, a point proximate the apex of the patient's heart, a point proximate the septal groove of the patient's heart, a point located on an object (e.g., leads, electrodes, devices) in the heart, etc.

Figure 6A:
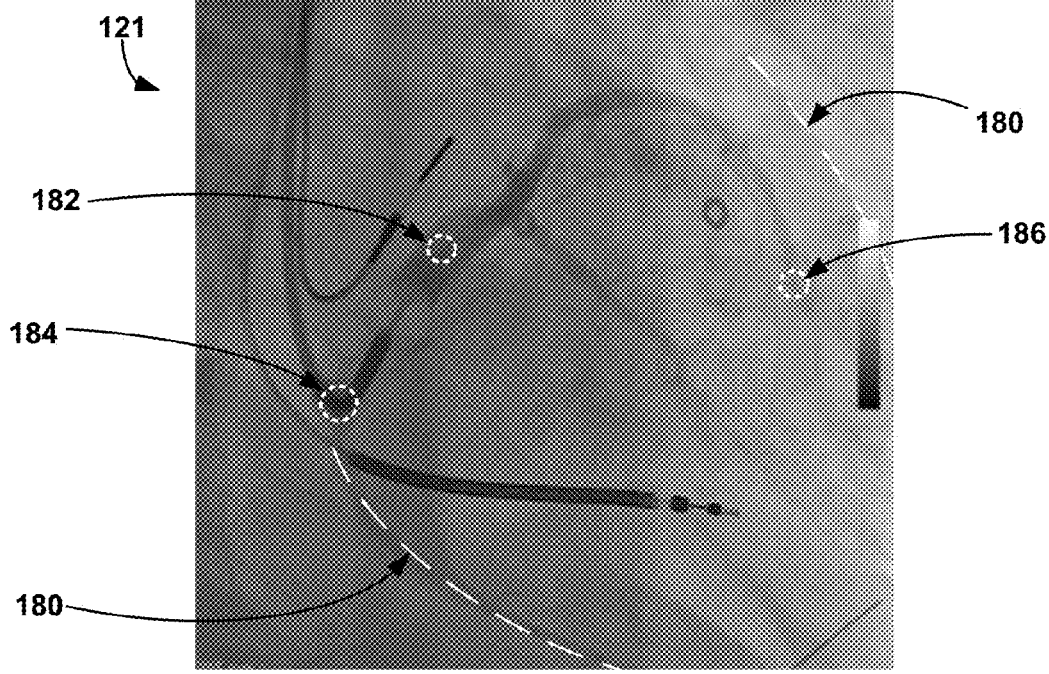
FIG. 6A depicts one or more detected features identified on the image of the heart of FIG. 3A.
Figure 6B:
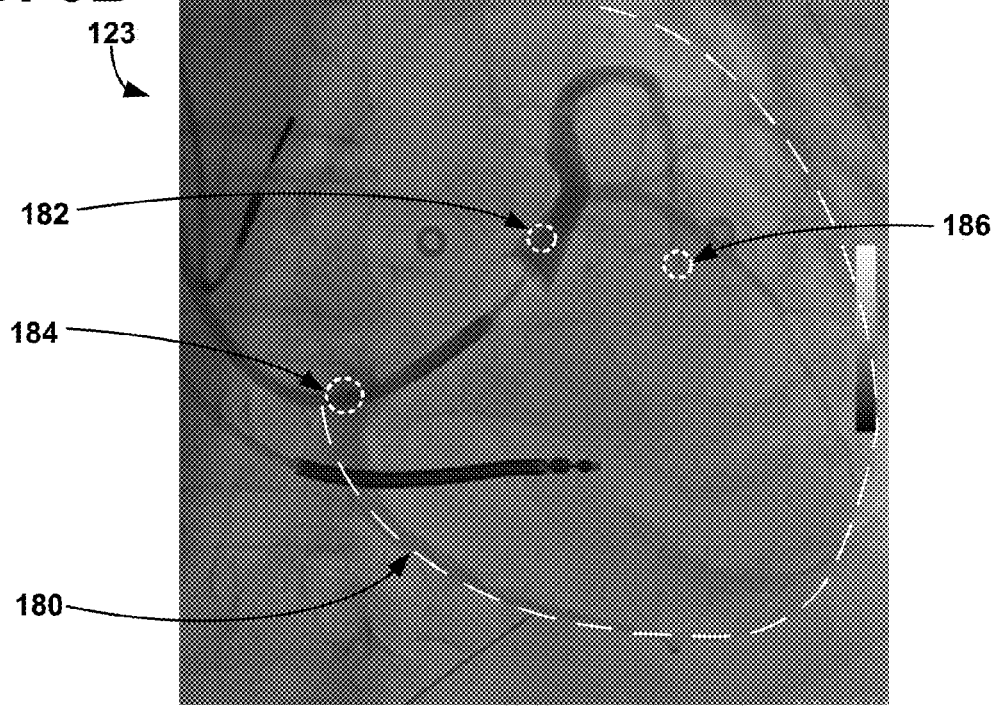
FIG. 6B depicts one or more detected features identified on the image of the heart of FIG. 3B.

Exemplary detected features are shown and identified on the images of the heart of FIGS. 3A-3B in FIGS. 6A-6B. As shown, the epicardial border 180, a point proximate an intersection between the middle cardiac vein (MCV) and the coronary sinus of the patient's heart 184, a right ventricular (RV) insertion point 182, and a distal point of the anterior interventricular vein (AIV) 186 are identified.

Figure 7:
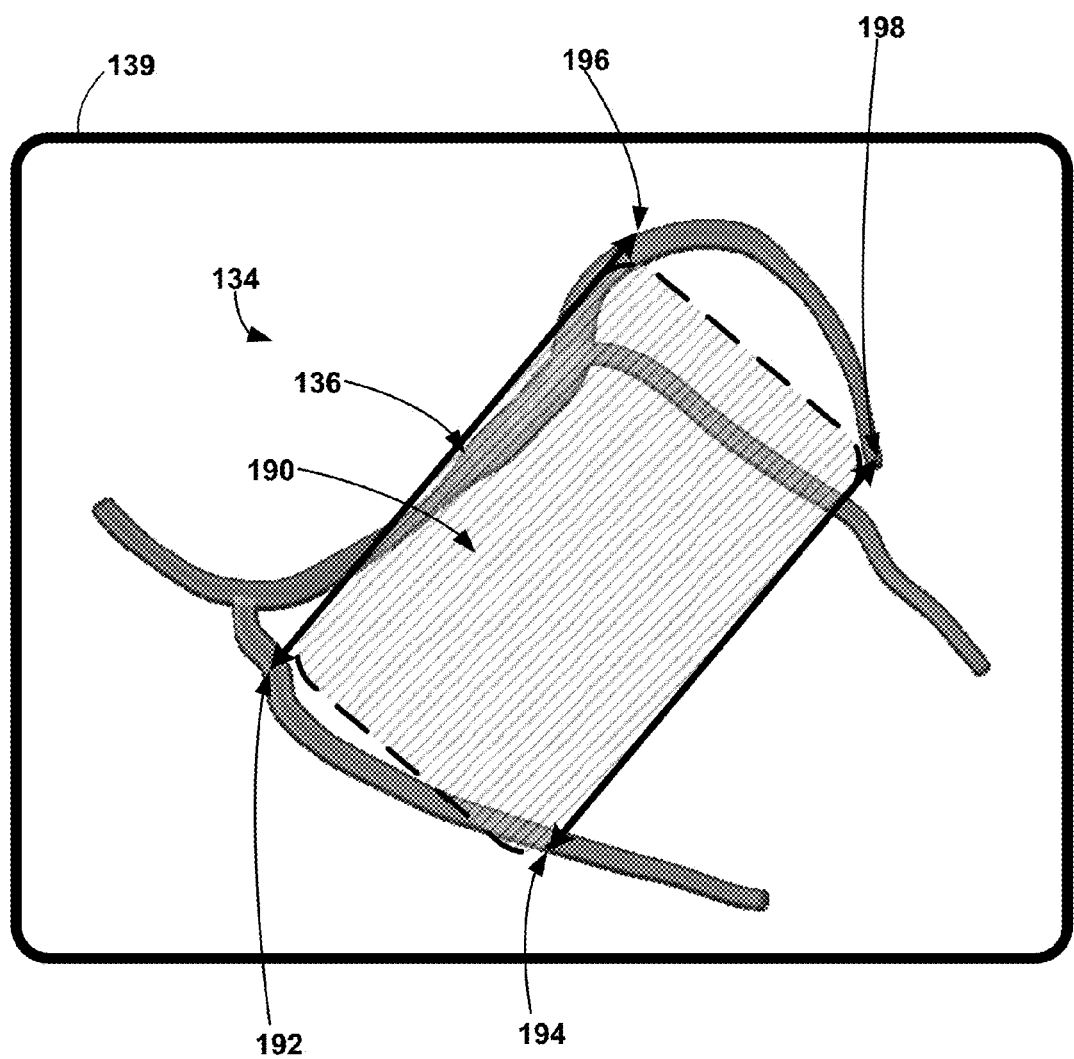
FIG. 7 depicts one or more detected features and a curved septal plane identified on the graphical representation of a portion of the blood vessel anatomy of the heart of FIG. 4.
Figure 8:
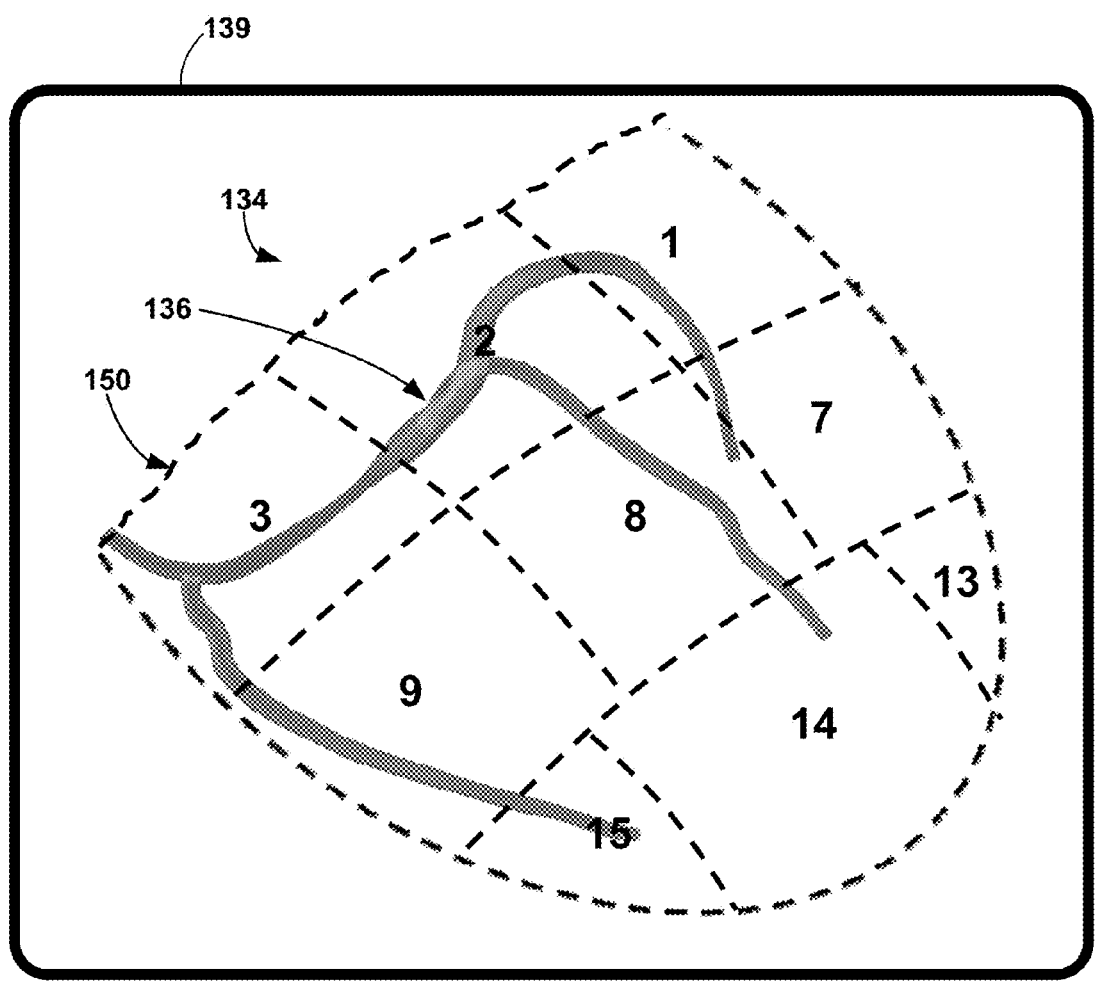
FIG. 8 depicts a phrenic nerve stimulation map projected on the graphical representation of a portion of the blood vessel anatomy of the heart of FIG. 4.
Figure 9:
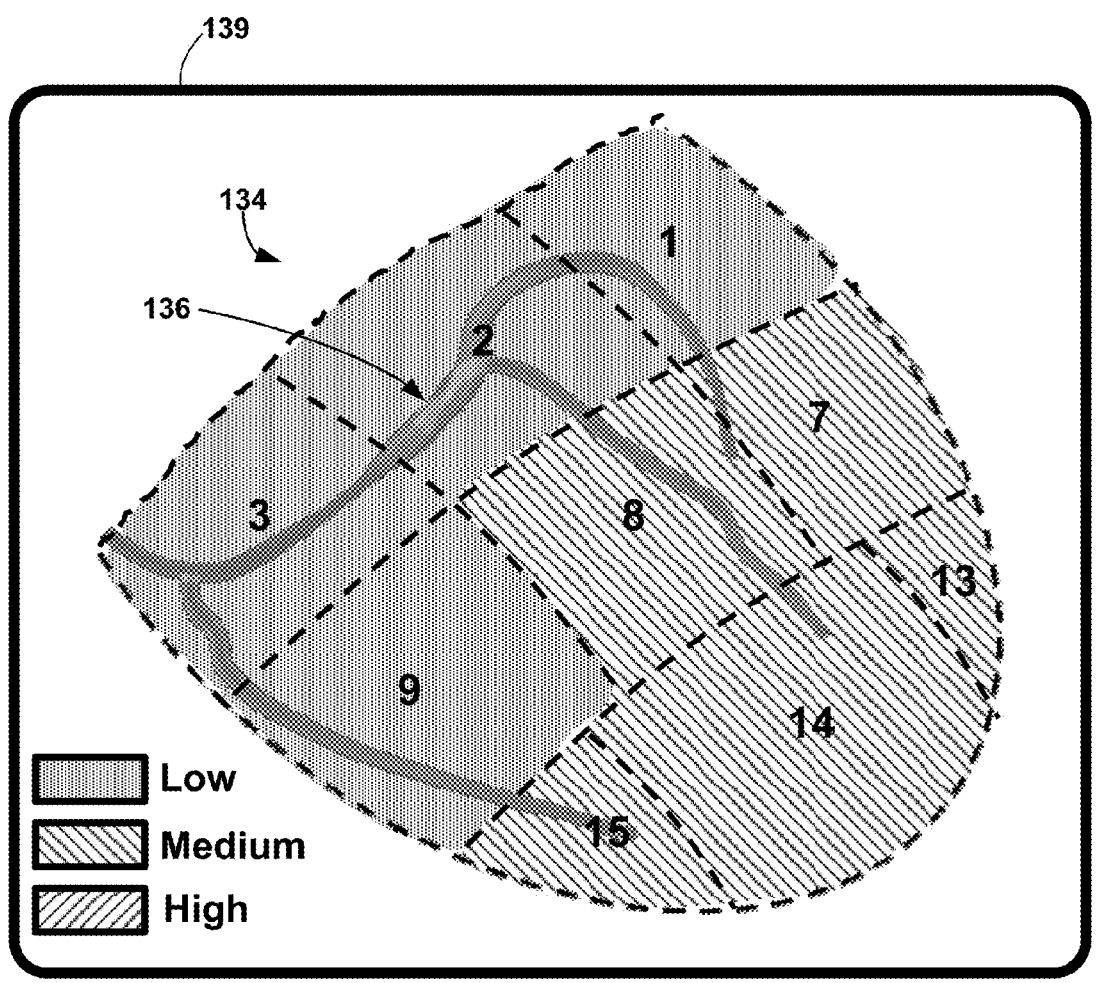
FIG. 9 depicts the phrenic nerve stimulation map of FIG. 5A projected on the graphical representation of a portion of the blood vessel anatomy of the heart of FIG. 4.

The identified features and/or one or more points proximate or along the one or more identified features may be used to project the phrenic nerve stimulation maps 150, 160 on a graphical representation 134 of the portion of blood vessel anatomy 136 of the patient's heart. To provide such functionality, the identified features and/or one or more points proximate or along the one or more identified features may be identified on the graphical representation 134 of the portion of blood vessel anatomy 136 of the patient's heart as shown in FIG. 7.

Further, a septal plane curve 190 may be defined by or between three or more points. As shown in FIG. 7, the septal plane curve 190 is defined between two points along the middle cardiac vein (MCV) and two points along the anterior interventricular vein (AIV). More specifically, the two points along the MCV include a bifurcation point 192 and a more distal point 194 (e.g., more distal than the bifurcation point). And, the two points along the AIV include a proximal point 196 and a more distal point 198 (e.g., more distal than the proximal point).

Based on the detected features of the patient's heart, the exemplary method 200 may project a phrenic nerve stimulation map onto a graphical representation of at least a portion of the patient's heart 210. The exemplary phrenic nerve stimulation map 150 of FIG. 5A is shown projected on the graphical representation 134 of a portion of the blood vessel anatomy 136 of the heart in FIG. 8. In this figure, no phrenic nerve stimulation is shown such that the segmentation of the areas 152 of the map 150 may be shown more clearly. The exemplary phrenic nerve stimulation map 150 of FIG. 5A including phrenic nerve stimulation information is shown projected on the graphical representation 134 of a portion of the blood vessel anatomy 136 of the heart in FIG. 9. Further, as before, the graphical representation 134 of the patient's heart and the projected phrenic nerve stimulation map 150 may be displayed using a graphical user interface 139 on display apparatus.

Although the phrenic nerve stimulation map is described herein as being projected onto a graphical representation of at least a portion of the patient's heart, it is to be understood that the combination of the phrenic nerve stimulation map and graphical representation of at least a portion of the patient's heart may be described many different ways. For example, the phrenic nerve stimulation map may be described as being mapped onto a graphical representation of at least a portion of the patient's heart (e.g., mapped according to the corresponding features). Further, for example, the graphical representation of at least a portion of the patient's heart may be described as being augmented with the phrenic nerve stimulation map. Further, for example, the graphical representation of at least a portion of the patient's heart may be described as being overlaid with the phrenic nerve stimulation map.

Although the graphical representation 134 of the patient's heart and the projected phrenic nerve stimulation map 150 as shown are two dimensional, it is to be understood that graphical representation 134 and the projected phrenic nerve stimulation map 150 may be displayed as a three dimensional image and/or a plurality of different two dimensional images (e.g., each two dimensional image from a different direction or angle). Further, a user (e.g., a physician) may use input apparatus to manipulate (e.g., rotate, change views, etc.) the graphical representation 134 and the projected phrenic nerve stimulation map 150.

Further, although the projected phrenic nerve stimulation map 150 as shown is a segmented map projected onto, or about, the graphical representation 134 of the patient's heart, it is to be understood that the phrenic nerve stimulation map 150 may be represented in many different ways relative to, or about, many different portions of a patient's heart. For example, the projected phrenic nerve stimulation map 150 may be color-coded, or use any other type of indication, along portions of the blood vessel anatomy of the patient's heart (e.g., the graphical representation, or depiction, of the blood vessel may be colored according to the phrenic nerve stimulation information from the phrenic nerve stimulation map). Further, only portions of blood vessels corresponding to the indications may be displayed.

As described herein, a user may use the exemplary systems, methods, and interfaces to configure cardiac therapy. More specifically, a user can use the graphical representation 134 and the projected phrenic nerve stimulation map 150 displayed on a graphical user interface 139 when selecting a pacing location (e.g., a location to deliver pacing therapy). For example, the exemplary systems, methods, and interfaces may assist a user in the navigation of one or more implantable electrodes to one or more regions of the patient's heart. For example, the exemplary systems, methods, and interfaces described herein may assist a user in the configuration of pacing vectors using already-implanted electrodes (e.g., anode(s) and cathode(s)) to deliver pacing therapy to one or more regions of the patient's heart.

Further, as described herein, it may not be desirable to deliver cardiac pacing therapy to regions of the patient's heart that may stimulate the patient's phrenic nerve. Thus, a user may use the graphical representation 134 and the projected phrenic nerve stimulation map 150 to identify regions where cardiac pacing therapy should be avoided to potentially avoid phrenic nerve stimulation (such as, e.g., the apex, or apical region, of the patient's heart).

During cardiac therapy adjustment, phrenic nerve stimulation may be detected. For example, the exemplary systems and methods may detect phrenic nerve stimulation in response to the presently-delivered cardiac therapy. Phrenic nerve stimulation detection may be described in U.S. patent application Ser. No. 14/220,733 filed on Mar. 20, 2014 and entitled "NON-INVASIVE DETECTION OF PHRENIC NERVE STIMULATION," U.S. Pat. App. Pub. No. 2012/0296388 A1 filed on May 17, 2012 and entitled "PHRENIC NERVE STIMULATION DETECTION USING HEART SOUNDS" and U.S. Pat. App. Pub. No. 2012/0296387 A1 filed on Nov. 22, 2012 and entitled "PHRENIC NERVE STIMULATION DETECTION USING HEART SOUNDS, each of which is incorporated herein by reference in its entirety. Further, for example, a patient may indicate to a user (e.g., physician) that phrenic nerve stimulation is occurring during a follow-up appointment. A user (e.g., physician) may also determine phrenic nerve stimulation through visual or tactile means.

Figure 10A:
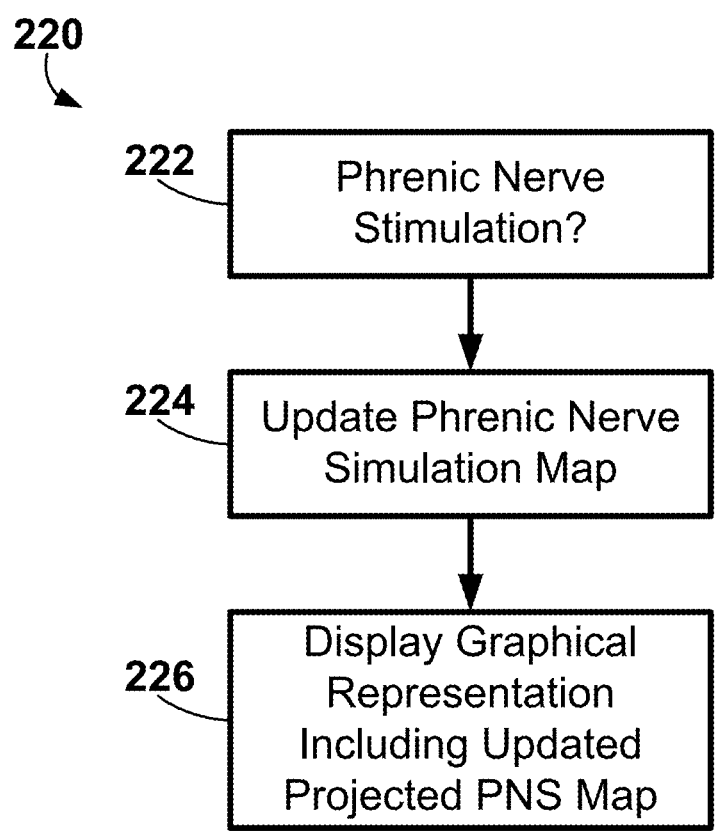
FIG. 10A is block diagram of an exemplary method of updating a phrenic nerve stimulation map.

The phrenic nerve stimulation map (for that particular patient) may be updated based on the detected or identified phrenic nerve stimulation. An exemplary method 220 of updating a phrenic nerve stimulation map is depicted in FIG. 10A. The method 220 may include determining whether phrenic nerve stimulation is occurring 222, which as described herein, may be determined automatically or input by a user. If the phrenic nerve stimulation is input by a user, the user may select one or more areas of a projected phrenic nerve stimulation map 150 as shown in FIGS. 5A-5B and/or with a graphical representation 134 of a portion of the patient's heart to be updated to indicate phrenic nerve stimulation is occurring in the selected region.

Figure 11:
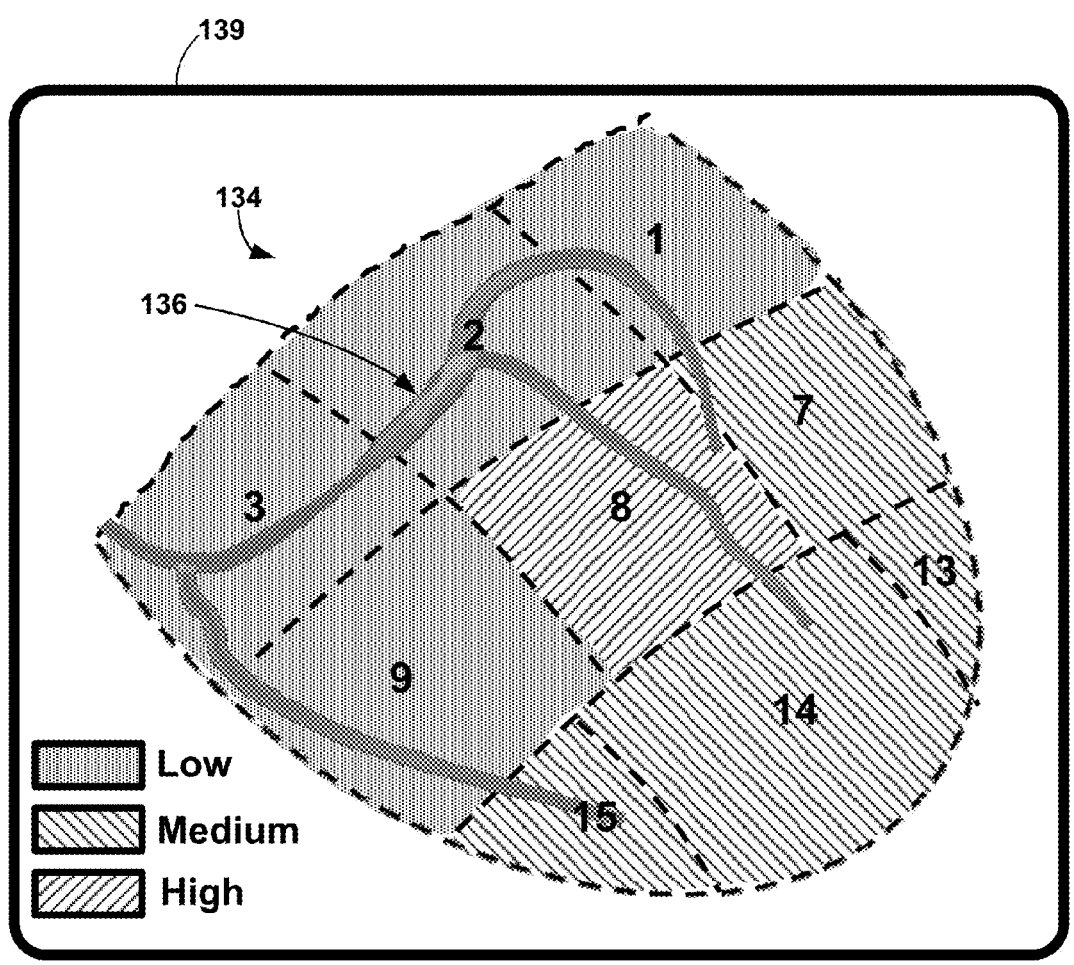
FIG. 11 depicts the phrenic nerve stimulation map of FIG. 5A after being updated and projected on the graphical representation of a portion of the blood vessel anatomy of the heart of FIG. 4.
Figure 12:
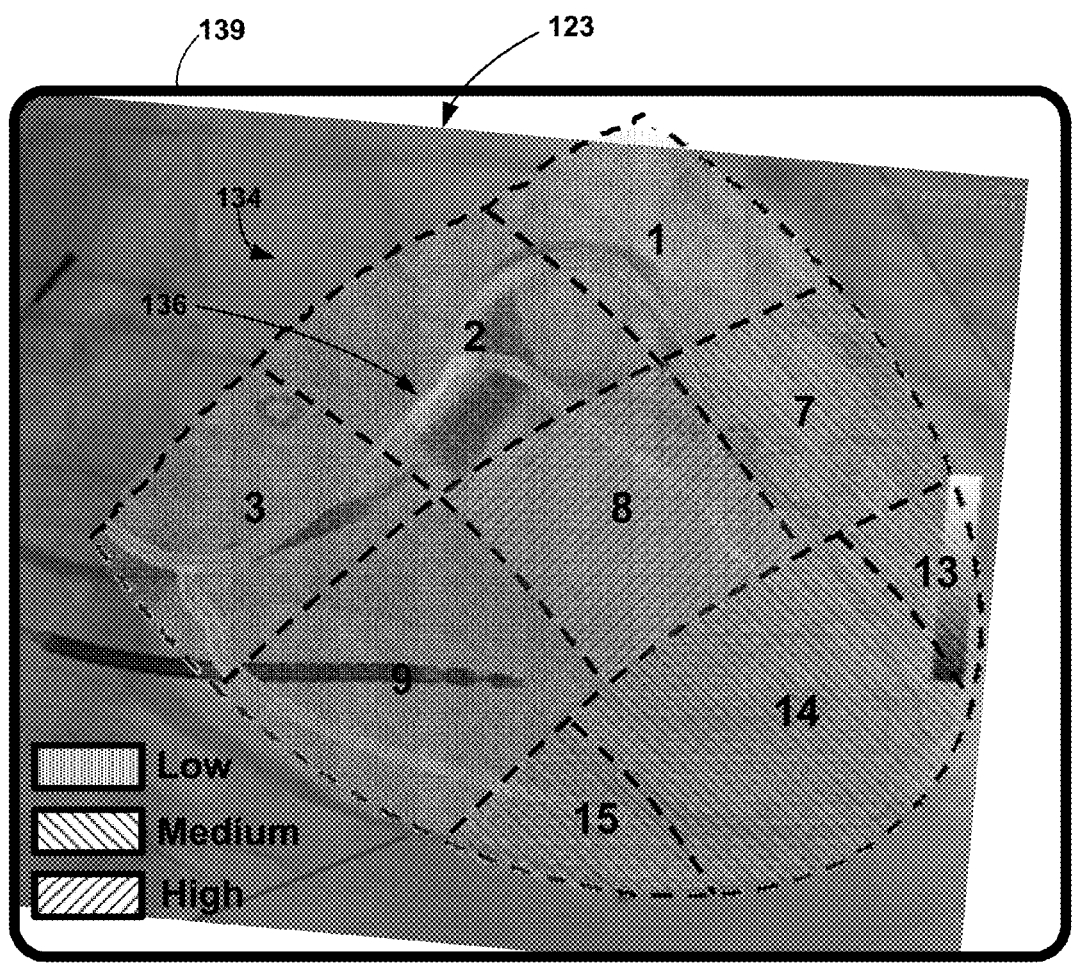
FIG. 12 depicts the phrenic nerve stimulation map of FIG. 5A after being updated and projected on the graphical representation of a portion of the blood vessel anatomy of the heart of FIG. 4 overlaying the image of patient's heart of FIG. 3B.

The exemplary method 220 may then update the phrenic nerve stimulation map 224 and may display the updated graphical representation and the phrenic nerve stimulation map 226. For example, a user may want to update the mid-anteroseptal area 8 of the phrenic nerve stimulation map 150 of FIGS. 5A and 9 to have a high indication, or likelihood, of phrenic nerve stimulation. To do so, the user may select the mid-anteroseptal area 8 and change the phrenic nerve stimulation information for that area. If the input apparatus 142 is a touchscreen, the user may touch the identified area 8 with their finger or stylus. Further, if the input apparatus 142 is a mouse, a user may "click on" the identified area 8 using the mouse. After the anteroseptal area 8 has been changed to a high indication of phrenic nerve stimulation, the graphical representation and the phrenic nerve stimulation map may be updated 224 and displayed 226 as shown in FIG. 11.

The graphical representation of a portion of a patient's heart and the phrenic nerve stimulation map may further be displayed, or presented, to a user in conjunction, or with, one or more images of the patient's heart (e.g., the captured images used to generate the graphical representation of a portion of the patient's heart). For example, the phrenic nerve stimulation map and the graphical representation of a portion of the blood vessel anatomy of the heart of FIG. 11 are shown overlaying, or depicted on or with, the image 123 of the patient's heart of FIG. 3B in FIG. 12. Additionally, the image 123 may be a real-time fluoroscopic image such that a user may visualize the implantation and navigation of one or more leads and electrodes to one or more portions of the patient's heart.

Figure 10B:
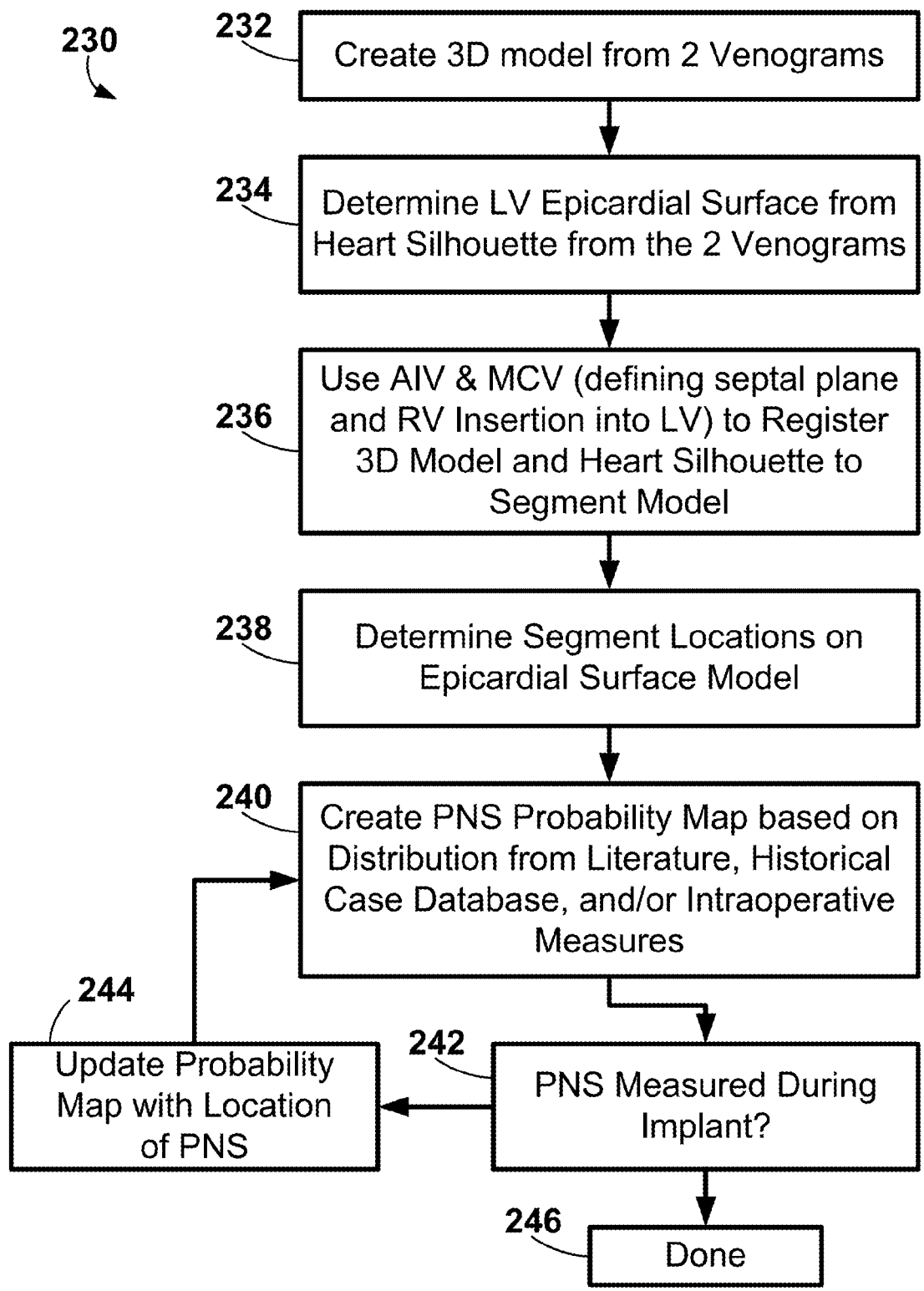
FIG. 10B is block diagram of an exemplary method of projecting and updating a phrenic nerve stimulation map.

Another exemplary method 230 of projecting and updating a phrenic nerve stimulation map is depicted in FIG. 10B. The exemplary method 230 includes creating a three-dimensional model of a portion of the patient's heart from two or more venograms 232 (e.g., venograms captured using the imaging apparatus described herein) and determining the left ventricular epicardial surface the heart silhouette from the two venograms 234. The exemplary method 230 further includes using the AIV and MCV to register the three-dimensional model and heart silhouette to a phrenic nerve stimulation segment model 236. For example, a septal plane may be defined by the AIV and the MCV used to define the RV insertion into LV location.

The exemplary method 230 further includes determining segment locations on the epicardial surface model 238 of the patient's heart and creating a phrenic nerve stimulation probability map based on distribution from literature, historical case database, and/or intraoperative measures 240. If phrenic nerve stimulation is detected during implant 242, the exemplary method 230 may update the probability map with the location of the phrenic nerve stimulation 244, and re-create the phrenic nerve stimulation probability map 240. If phrenic nerve stimulation is not detected during implant 242, the exemplary method 230 may be done 246.

Although the exemplary methods, systems, and interfaces are described herein with respect to phrenic nerve stimulation, it is to be understood that many different types of data may be projected, or added, to graphical representations of the patient's heart or other body portions using the same or similar exemplary methods, systems, and interfaces. For example, instead of, or in conjunction with, the phrenic nerve stimulation map, the exemplary methods, systems, and interfaces may use a scar risk map that includes a plurality of areas corresponding to different regions of a human heart, and each area of the plurality of areas may be configured to provide scar risk information for the corresponding region of the human heart (e.g., likelihood of scar in response to delivery of pacing therapy). Further, for example, the exemplary methods, systems, and interfaces may use dyssynchrony information projected about a graphical representation of the patient's heart. Further, the exemplary methods, systems, and interfaces may use electrical timing information projected about a graphical representation of the patient's heart.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 13-15.

Figure 13:
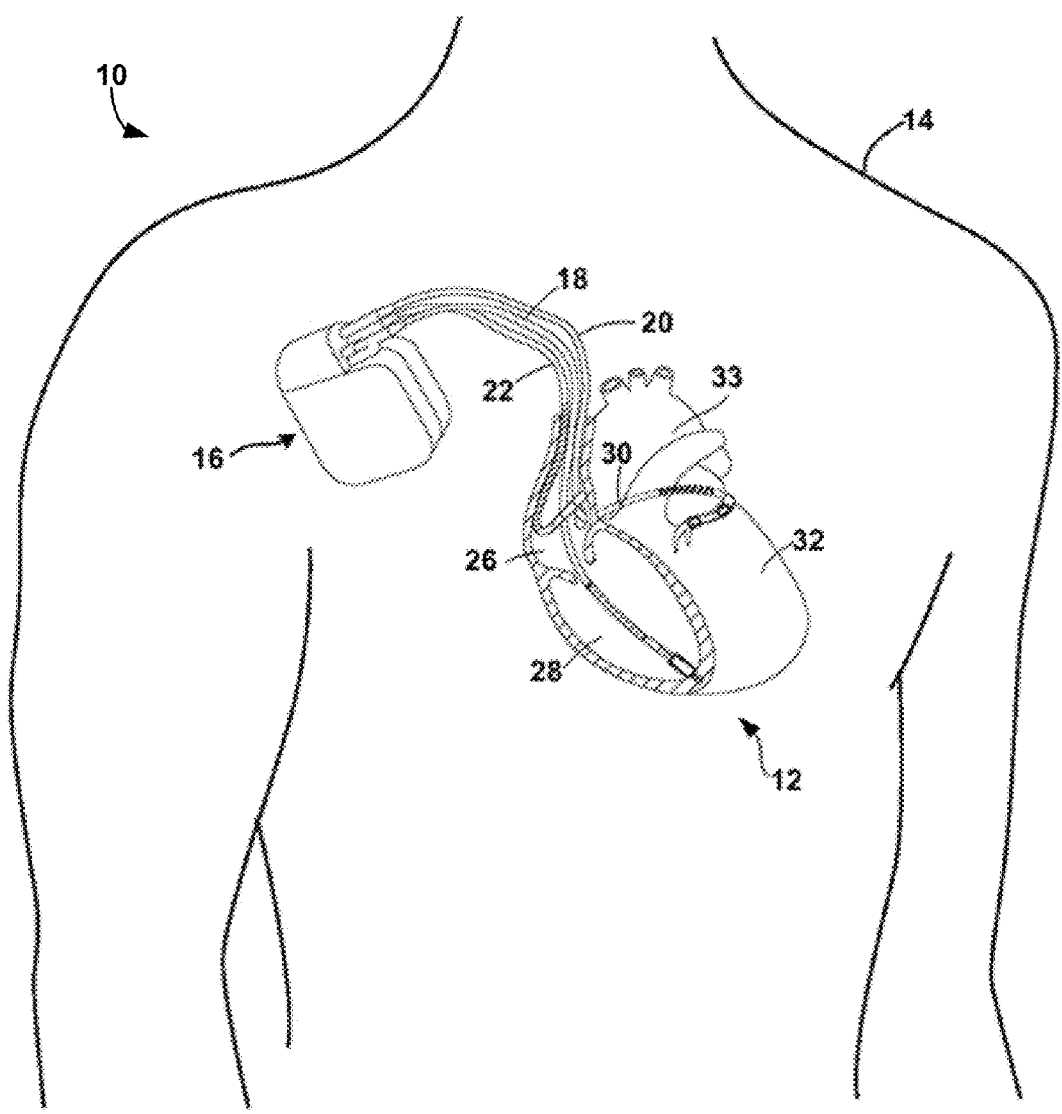
FIG. 13 is a diagram of an exemplary system including an exemplary implantable medical device (IMD).

FIG. 13 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 13, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 14A:
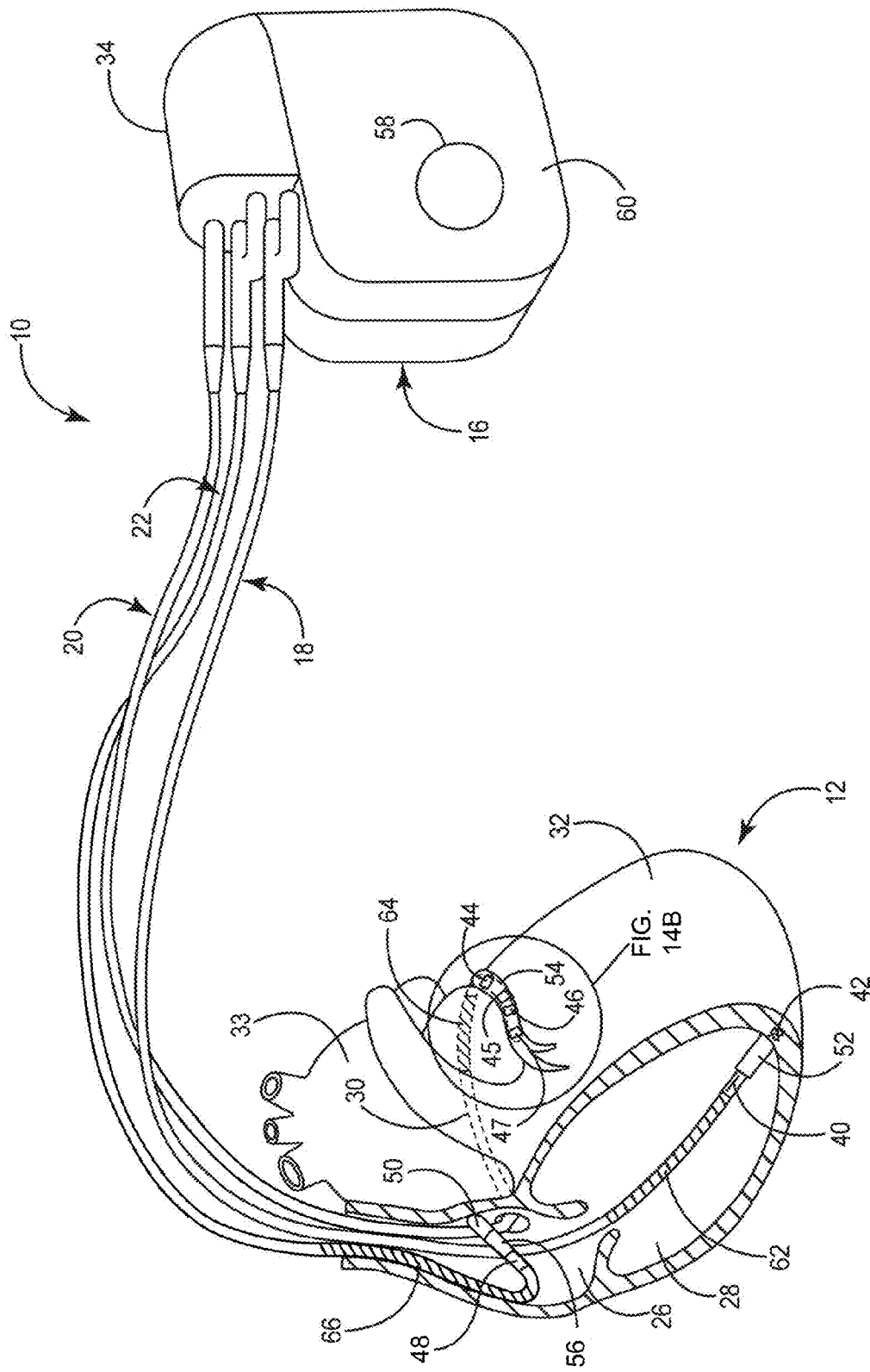
FIG. 14A is a diagram of the exemplary IMD of FIG. 13.
Figure 14B:
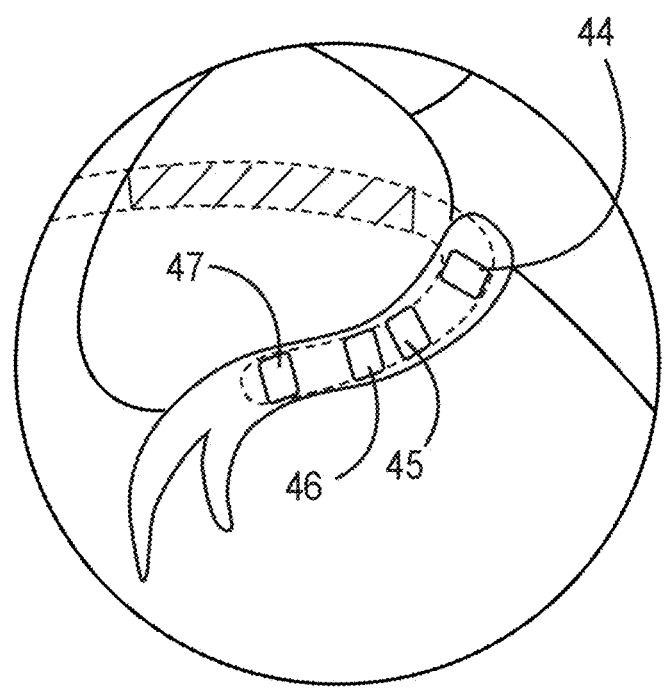
FIG. 14B is a diagram of an enlarged view of a distal end of the electrical lead disposed in the coronary vein on the left ventricle of FIG. 14A.

FIGS. 14A-14B are conceptual diagrams illustrating the IMD 16 and the leads 18, 20, 22 of therapy system 10 of FIG. 13 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 $mm^2$ to about 5.8 $mm^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 14A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 14A, the housing 60 may enclose a therapy delivery module that may include a stimulation generator for generating cardiac pacing pulses and defibrillation or cardioversion shocks, as well as a sensing module for monitoring the electrical signals of the patients heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 13-15 is merely one example. In other examples, the therapy system may include epicardial leads and/or patch electrodes instead of or in addition to the transvenous leads 18, 20, 22 illustrated in FIG. 13. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 13). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 13-15. Still further, other therapy systems may include a single lead that extends from the IMD 16 into the right atrium 26 or the right ventricle 28, or two leads that extend into a respective one of the right atrium 26 and the right ventricle 28.

Figure 15A:
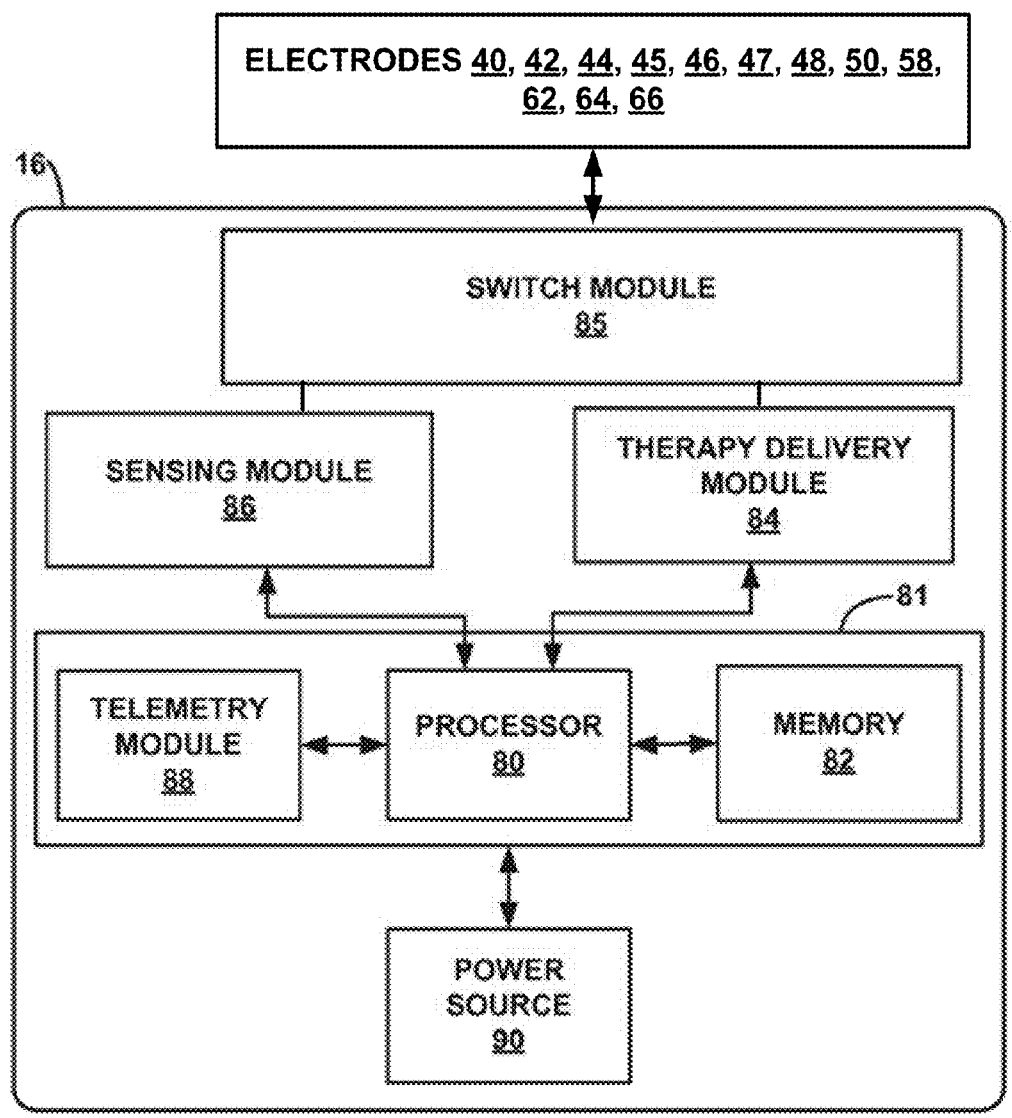
FIG. 15A is a block diagram of an exemplary IMD, e.g., of the system of FIGS. 13-14.

FIG. 15A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 15B:
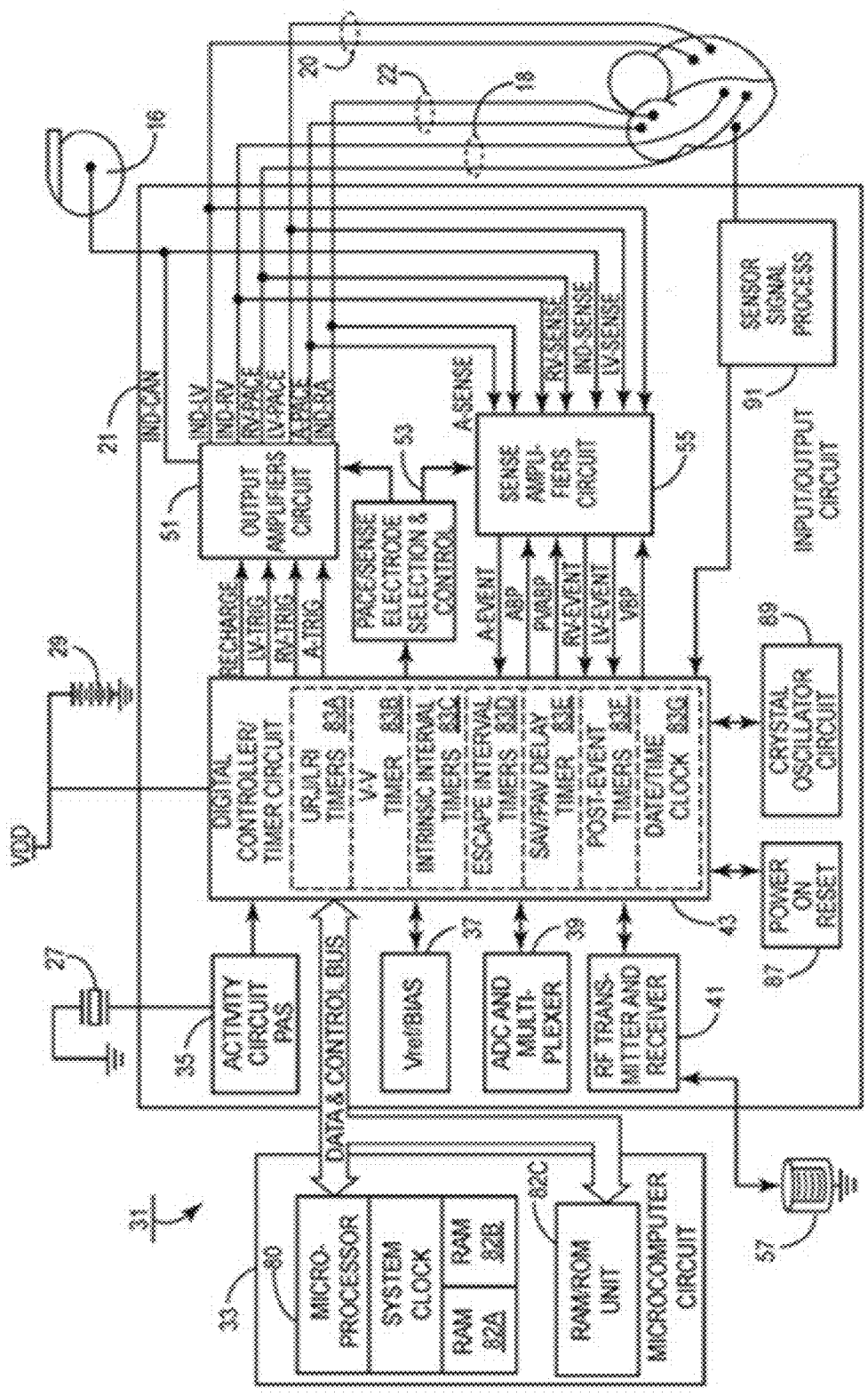
FIG. 15B is another block diagram of an exemplary IMD (e.g., an implantable pulse generator) circuitry and associated leads, e.g., employed in the systems of FIGS. 13-14.

FIG. 15B is another embodiment of a functional block diagram for IMD 16. FIG. 15B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A system for assisting a user in configuring cardiac therapy comprising:
 a display apparatus comprising a graphical user interface, wherein the graphical user interface is configured to depict at least a portion of a patient's heart; and
 computing apparatus coupled to display apparatus and configured to provide the graphical user interface displayed on the display apparatus to assist a user in selecting a pacing location, wherein the computing apparatus is further configured to:
 provide one or more images of the patient's heart,
 provide a phrenic nerve stimulation map comprising a plurality of areas corresponding to different regions of a human heart, wherein each area of the plurality of areas is configured to provide phrenic nerve stimulation information for the corresponding region of the human heart,
 detect one or more features of the patient's heart within and based on the one or more images of the patient's heart,
 project the phrenic nerve stimulation map on a graphical representation of at least a portion of the patient's heart based on the one or more detected features of the patient's heart, and
 display, on the graphical user interface, the graphical representation of at least a portion of the patient's heart and the projected phrenic nerve stimulation map.

2. The system of claim 1, wherein the one or more features of the patient's heart comprise at least one of an epicardial border of the patient's heart, the middle cardiac vein of the patient's heart, the anterior interventricular vein of the patient's heart, the interventricular septum of the patient's heart, and the coronary sinus of the patient's heart.

3. The system of claim 1, wherein the graphical representation of at least a portion of the patient's heart comprises at least a portion of the blood vessel anatomy of the patient's heart.

4. The system of claim 1, wherein the plurality of areas of the phrenic nerve stimulation map correspond to different regions of the left ventricle of the human heart.

5. The system of claim 1, wherein projecting the phrenic nerve stimulation map on the graphical representation of at least a portion of the patient's heart based on the one or more detected features of the patient's heart comprises defining a plane curve based on a plurality of points identified in the one or more detected features of the patient's heart.

6. The system of claim 5, wherein the plurality of points identified in the detected one or more features of the patient's heart comprise one or more of:
a point proximate an intersection between the middle cardiac vein and the coronary sinus of the patient's heart;
a point along the middle cardiac vein;
a point proximate a distal end of the anterior interventricular vein of the patient's heart;
a point along the anterior interventricular vein of the patient's heart;
a point proximate the apex of the patient's heart; and
a point proximate the septal groove of the patient's heart.

7. The system of claim 1, wherein the phrenic nerve stimulation information of the plurality of areas of the phrenic nerve stimulation map comprises a probability map defining an indication of likelihood of phrenic nerve stimulation in response to pacing therapy delivered to the corresponding region of the human heart.

8. The system of claim 7, wherein the indication of likelihood of phrenic nerve stimulation in response to pacing therapy delivered to the corresponding region of the human heart comprises one of a high indication of phrenic nerve stimulation, a medium indication of phrenic nerve stimulation, and a low indication of phrenic nerve stimulation.

9. The system of claim 1, wherein the plurality of areas of the phrenic nerve stimulation map are color-coded to provide an indication of likelihood of phrenic nerve stimulation in response to pacing therapy delivered to the corresponding regions of the human heart.

10. The system of claim 1, wherein the plurality of areas of the phrenic nerve stimulation map comprises 17 or less areas.

11. The system of claim 1, wherein the system further comprises imaging apparatus configured to image the patient's heart, and wherein the computing apparatus is further configured to capture the one or more images of the patient's heart using the imaging apparatus, wherein the graphical representation of at least a portion of the patient's heart is generated based on the one or more images.

12. The system of claim 1, wherein the computing apparatus is further configured to display at least one image of the one or more images of the patient's heart proximate the graphical representation of at least a portion of the patient's heart and the projected phrenic nerve stimulation map.

13. The system of claim 12, wherein the graphical representation of at least a portion of the patient's heart and the projected phrenic nerve stimulation map overlay the displayed at least one image of the one or more images of the patient's heart.

14. The system of claim 1, wherein the computing apparatus is further configured to generate the graphical representation of at least a portion of the patient's heart based on one or more images of the patient's heart.

15. The system of claim 1, wherein the graphical representation of at least a portion of the patient's heart and the projected phrenic nerve stimulation map displayed on the graphical user interface is a three-dimensional graphical representation.

16. The system of claim 1, wherein the computing apparatus is further configured to:
allow a user to update the phrenic nerve stimulation information in an area of the plurality of areas of the phrenic nerve stimulation map; and
display, on the graphical user interface, the graphical representation of at least a portion of the patient's heart and the projected phrenic nerve stimulation map including the updated phrenic nerve stimulation information.

17. The system of claim 1, wherein the computing apparatus is further configured to:
detect phrenic nerve stimulation at a pacing location;
update the phrenic nerve stimulation information in an area of the plurality of areas of the phrenic nerve stimulation map corresponding to the pacing location; and
display, on the graphical user interface, the graphical representation of at least a portion of the patient's heart and the projected phrenic nerve stimulation map including the updated phrenic nerve stimulation information.

18. A method for assisting a user in configuring cardiac therapy comprising:
providing one or more images of a patient's heart,
providing a phrenic nerve stimulation map comprising a plurality of areas corresponding to different regions of a human heart, wherein each area of the plurality of areas is configured to provide phrenic nerve stimulation information for the corresponding region of the human heart,
detecting one or more features of the patient's heart within and based on the one or more images of the patient's heart,
projecting the phrenic nerve stimulation map on a graphical representation of at least a portion of the patient's heart based on the one or more detected features of the patient's heart, and
displaying, on a graphical user interface, the graphical representation of at least a portion of the patient's heart and the projected phrenic nerve stimulation map.

19. The method of claim 18, wherein the one or more features of the patient's heart comprise at least one of an epicardial border of the patient's heart, the middle cardiac vein of the patient's heart, the anterior interventricular vein of the patient's heart, the interventricular septum of the patient's heart, and the coronary sinus of the patient's heart.

20. The method of claim 18, wherein the graphical representation of at least a portion of the patient's heart comprises at least a portion of the blood vessel anatomy of the patient's heart.

21. The method of claim 18, wherein the plurality of areas of the phrenic nerve stimulation map correspond to different regions of the left ventricle of the human heart.

22. The method of claim 18, wherein projecting the phrenic nerve stimulation map on the graphical representation of at least a portion of the patient's heart based on the one or more detected features of the patient's heart comprises defining a plane curve based on a plurality of points identified in the one or more detected features of the patient's heart.

23. The method of claim 22, wherein the plurality of points identified in the detected one or more features of the patient's heart comprise one or more of:
a point proximate an intersection between the middle cardiac vein and the coronary sinus of the patient's heart;
a point along the middle cardiac vein;

a point proximate a distal end of the anterior interventricular vein of the patient's heart;
a point along the anterior interventricular vein of the patient's heart;
a point proximate the apex of the patient's heart; and
a point proximate the septal groove of the patient's heart.

24. The method of claim 18, wherein the phrenic nerve stimulation information of the plurality of areas of the phrenic nerve stimulation map comprises a probability map defining an indication of likelihood of phrenic nerve stimulation in response to pacing therapy delivered to the corresponding region of the human heart.

25. The method of claim 18, wherein the indication of likelihood of phrenic nerve stimulation in response to pacing therapy delivered to the corresponding region of the human heart comprises one of a high indication of phrenic nerve stimulation, a medium indication of phrenic nerve stimulation, and a low indication of phrenic nerve stimulation.

26. The method of claim 18, wherein the plurality of areas of the phrenic nerve stimulation map are color-coded to provide an indication of likelihood of phrenic nerve stimulation in response to pacing therapy delivered to the corresponding regions of the human heart.

27. The method of claim 18, wherein the plurality of areas of the phrenic nerve stimulation map comprises 17 or less areas.

28. The method of claim 18, wherein the method further comprises capturing the one or more images of the patient's heart, wherein the graphical representation of at least a portion of the patient's heart is generated based on the one or more images.

29. The method of claim 18, wherein the method further comprises displaying at least one image of the one or more images of the patient's heart proximate the graphical representation of at least a portion of the patient's heart and the projected phrenic nerve stimulation map.

30. The method of claim 29, wherein the graphical representation of at least a portion of the patient's heart and the projected phrenic nerve stimulation map overlay the displayed at least one image of the one or more images of the patient's heart.

31. The method of claim 18, wherein the method further comprises generating the graphical representation of at least a portion of the patient's heart based on the one or more images of the patient's heart.

32. The method of claim 18, wherein the graphical representation of at least a portion of the patient's heart and the projected phrenic nerve stimulation map displayed on the graphical user interface is a three-dimensional graphical representation.

33. The method of claim 18, wherein the method further comprises:
allowing a user to update the phrenic nerve stimulation information in an area of the plurality of areas of the phrenic nerve stimulation map; and
displaying, on the graphical user interface, the graphical representation of at least a portion of the patient's heart and the projected phrenic nerve stimulation map including the updated phrenic nerve stimulation information.

34. The method of claim 18, wherein the method further comprises:
detecting phrenic nerve stimulation at a pacing location;
updating the phrenic nerve stimulation information in an area of the plurality of areas of the phrenic nerve stimulation map corresponding to the pacing location; and
displaying, on the graphical user interface, the graphical representation of at least a portion of the patient's heart and the projected phrenic nerve stimulation map including the updated phrenic nerve stimulation information.

35. A system for assisting a user in configuring cardiac therapy comprising:
a display apparatus comprising a graphical user interface, wherein the graphical user interface is configured to depict at least a portion of a patient's heart; and
computing apparatus coupled to display apparatus and configured to provide the graphical user interface displayed on the display apparatus to assist a user in selecting a pacing location, wherein the computing apparatus is further configured to:
provide one or more images of the patient's heart,
provide an information map comprising a plurality of areas corresponding to different regions of a human heart, wherein each area of the plurality of areas is configured to provide information for the corresponding region of the human heart,
detect one or more features of the patient's heart within and based on the one or more images of the patient's heart,
project the information map on a graphical representation of at least a portion of the patient's heart based on the one or more detected features of the patient's heart, and
display, on the graphical user interface, the graphical representation of at least a portion of the patient's heart and the projected information map, wherein the information map comprises one or more of a phrenic nerve stimulation map, a scar risk map, a tissue viability map, and a tissue strain map.

36. The system of claim 35, wherein the information map further comprises one or more of an electrical timing map and a dyssynchrony map.

37. A method for assisting a user in configuring cardiac therapy comprising:
providing one or more images of a patient's heart,
providing an information map comprising a plurality of areas corresponding to different regions of a human heart, wherein each area of the plurality of areas is configured to provide information for the corresponding region of the human heart,
detecting one or more features of the patient's heart within and based on the one or more images of the patient's heart,
projecting the information map on a graphical representation of at least a portion of the patient's heart based on the one or more detected features of the patient's heart, and
displaying, on a graphical user interface, the graphical representation of at least a portion of the patient's heart and the projected information map, the information map comprises one or more of a phrenic nerve stimulation map, a scar risk map, a tissue viability map, a neighboring medical device map, and a contractility map.

38. A system for assisting a user in configuring cardiac therapy comprising:
a display apparatus comprising a graphical user interface, wherein the graphical user interface is configured to depict at least a portion of a patient's heart; and
computing apparatus coupled to display apparatus and configured to provide the graphical user interface displayed on the display apparatus to assist a user in selecting a pacing location, wherein the computing apparatus is further configured to:
provide one or more images of the patient's heart,
provide an information map comprising a plurality of areas corresponding to different regions of a human heart, wherein each area of the plurality of areas is configured to provide information for the corresponding region of the human heart,
detect one or more features of the patient's heart within and based on the one or more images of the patient's heart,
project the information map on a graphical representation of at least a portion of the patient's heart based on the one or more detected features of the patient's heart, and
display, on the graphical user interface, the graphical representation of at least a portion of the patient's heart and the projected information map, wherein the information map comprises one or more of a phrenic nerve stimulation map, a scar risk map, a tissue viability map, and a neighboring medical device map.

39. A system for assisting a user in configuring cardiac therapy comprising:
a display apparatus comprising a graphical user interface, wherein the graphical user interface is configured to depict at least a portion of a patient's heart; and
computing apparatus coupled to display apparatus and configured to provide the graphical user interface displayed on the display apparatus to assist a user in selecting a pacing location, wherein the computing apparatus is further configured to:
provide one or more images of the patient's heart,
provide an information map comprising a plurality of areas corresponding to different regions of a human heart, wherein each area of the plurality of areas is configured to provide information for the corresponding region of the human heart,
detect one or more features of the patient's heart within and based on the one or more images of the patient's heart,
project the information map on a graphical representation of at least a portion of the patient's heart based on the one or more detected features of the patient's heart, and
display, on the graphical user interface, the graphical representation of at least a portion of the patient's heart and the projected information map, wherein the information map comprises one or more of a phrenic nerve stimulation map, a scar risk map, and a tissue viability map.

40. A system for assisting a user in configuring cardiac therapy comprising:
a display apparatus comprising a graphical user interface, wherein the graphical user interface is configured to depict at least a portion of a patient's heart; and
computing apparatus coupled to display apparatus and configured to provide the graphical user interface displayed on the display apparatus to assist a user in selecting a pacing location, wherein the computing apparatus is further configured to:
provide one or more images of the patient's heart,
provide an information map comprising a plurality of areas corresponding to different regions of a human heart, wherein each area of the plurality of areas is configured to provide information for the corresponding region of the human heart,
detect one or more features of the patient's heart within and based on the one or more images of the patient's heart,
project the information map on a graphical representation of at least a portion of the patient's heart based on the one or more detected features of the patient's heart, and
display, on the graphical user interface, the graphical representation of at least a portion of the patient's heart and the projected information map, wherein the information map comprises a contractility map.

41. A system for assisting a user in configuring cardiac therapy comprising:
a display apparatus comprising a graphical user interface, wherein the graphical user interface is configured to depict at least a portion of the patient's heart; and
computing apparatus coupled to display apparatus and configured to provide the graphical user interface displayed on the display apparatus to assist a user in selecting a pacing location, wherein the computing apparatus is further configured to:
provide an information map comprising a plurality of areas corresponding to different regions of a human heart, wherein each area of the plurality of areas is configured to provide information for the corresponding region of the human heart,
detect one or more features of the patient's heart within one or more images of the patient's heart,
project the information map on a graphical representation of at least a portion of the patient's heart based on the one or more detected features of the patient's heart, and
display, on the graphical user interface, the graphical representation of at least a portion of the patient's heart and the projected information map, wherein the information map comprises a neighboring medical device map.

* * * * *